US009988358B2

(12) United States Patent
Heindl et al.

(10) Patent No.: US 9,988,358 B2
(45) Date of Patent: Jun. 5, 2018

(54) PHENAZINIUM MEDIATORS

(71) Applicant: Roche Diagnostics Operations, Inc., Indianapolis, IN (US)

(72) Inventors: Dieter Heindl, Munich (DE); Christine Nortmeyer, Mannheim (DE); Peter Gebauer, Penzberg (DE); Stacy H. Duvall, Indianapolis, IN (US); Klaus Andreas Bauer-Espindola, Mannheim (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 11 days.

(21) Appl. No.: 15/290,440

(22) Filed: Oct. 11, 2016

(65) Prior Publication Data
US 2017/0226068 A1 Aug. 10, 2017

Related U.S. Application Data

(63) Continuation of application No. PCT/EP2015/057933, filed on Apr. 13, 2015.

(30) Foreign Application Priority Data

Apr. 14, 2014 (EP) .................................. 14164571

(51) Int. Cl.
C07D 241/46 (2006.01)
C12Q 1/26 (2006.01)
(52) U.S. Cl.
CPC ............. C07D 241/46 (2013.01); C12Q 1/26 (2013.01)
(58) Field of Classification Search
CPC .................................................. C07D 241/46
USPC ........................................................ 544/348
See application file for complete search history.

(56) References Cited

U.S. PATENT DOCUMENTS

| | | | |
|---|---|---|---|
| 4,683,198 | A | 7/1987 | Ishikawa et al. |
| 4,919,770 | A | 4/1990 | Preidel et al. |
| 5,054,039 | A | 10/1991 | Blackmon et al. |
| 5,108,564 | A | 4/1992 | Szuminsky et al. |
| 5,801,006 | A | 9/1998 | Kaufman |
| 7,132,270 | B2 | 11/2006 | Kratzsch et al. |
| 7,547,535 | B2 | 6/2009 | Kratzsch et al. |
| 2005/0023152 | A1 | 2/2005 | Surridge et al. |
| 2009/0246808 | A1 | 10/2009 | Wilsey et al. |

FOREIGN PATENT DOCUMENTS

| | | |
|---|---|---|
| EP | 0821234 A2 | 1/1998 |
| EP | 0974303 B2 | 7/2006 |
| EP | 1660648 B1 | 10/2013 |
| WO | 1998/033936 A1 | 8/1998 |
| WO | 2001/049247 A2 | 7/2001 |
| WO | 2005/045016 A2 | 5/2005 |
| WO | 2007/012494 A1 | 2/2007 |
| WO | 2007/071562 A1 | 6/2007 |
| WO | 2009/103540 A1 | 8/2009 |
| WO | 2009/118157 A1 | 10/2009 |
| WO | 2014/001382 A1 | 1/2014 |

OTHER PUBLICATIONS

Baik, Sang-Ho et al., Cooperative Effect of Two Surface Amino Acid Mutations (Q252L and E170K) in Glucose Dehydrogenase from Bacillus megaterium IWG3 on Stabilization of Its Oligomeric State, Applied and Environmental Microbiology, 2005, pp. 3285-3293, vol. 71, No. 6.
Bünemann, H. et al., Synthesis and Properties of Acrylamide-Substituted Base Pair Specific Dyes for Deoxyribonucleic Acid Template Mediated Synthesis of Dye Polymers, Biochemistry, 1981, pp. 2864-2874, vol. 20, No. 10.
Cooney, M. J. et al., Enzyme catalysed biofuel cells, Energy & Environmental Science, 2008, pp. 320-337, vol. 1.
Ghosh, R. and Quayle, J. R., Phenazine Ethosulfate as a Preferred Electron Acceptor to Phenazine Methosulfate in Dye-Linked Enzyme Assays, Analytical Biochemistry, 1979, pp. 112-117, vol. 99.
Habermüller, Katja et al., Electron-transfer mechanisms in amperometric biosensors, Fresenius Journal of Analytical Chemistry, 2000, pp. 560-568, vol. 366.
Heller, Adam and Feldman, Ben, Electrochemical Glucose Sensors and Their Applications in Diabetes Management, Chemical Reviews, 2008, pp. 2482-2505, vol. 108.
Hisada, Ryuki et al., Photochemical Stabilities and Biochemical Reactivities of Some Derivatives of 5-Methylphenazinium Methyl Sulfate (Phenazine Methosulfate), Journal of Applied Biochemistry, 1981, pp. 535-543, vol. 3.
Hutchinson, Edward J. et al., Synthesis of carbocyclic NAD+ containing a methylenebisphosphonate linkage for the investigation of ADP-ribosyl cyclase, Chemical Communications, 1996, pp. 2765-2766, vol. 24.
Hönes, Joachim et al., The Technology Behind Glucose Meters: Test Strips, Diabetes Technology & Therapeutics, 2008, pp. S-10-S-26, vol. 10, Supplement 1.
International Search Report dated Jun. 1, 2015, in Application No. PCT/EP2015/057933, 4 pages.
Inzelt, G. and Puskás, Z., Adsorption and precipitation during the redox transformations of phenazine, Electrochimica Acta, 2004, pp. 1969-1980, vol. 49.

(Continued)

*Primary Examiner* — Deepak R Rao
(74) *Attorney, Agent, or Firm* — Woodard, Emhardt, Moriarty, McNett & Henry LLP

(57) ABSTRACT

The present invention relates to a chemical compound or a salt or solvate thereof being an 1-amino-phenazine derivative and to uses thereof. The present invention further relates to a chemistry matrix and to a test element comprising the aforesaid chemical compound. Moreover, the present invention relates to a method for determining the amount of an analyte in a sample, comprising contacting said sample with a chemistry matrix according to the present invention, estimating the amount of electrons liberated or consumed by the chemistry matrix in the presence of said liquid sample, and thereby determining the amount of an analyte in a liquid sample.

15 Claims, 5 Drawing Sheets

(56) References Cited

OTHER PUBLICATIONS

Figure 1:
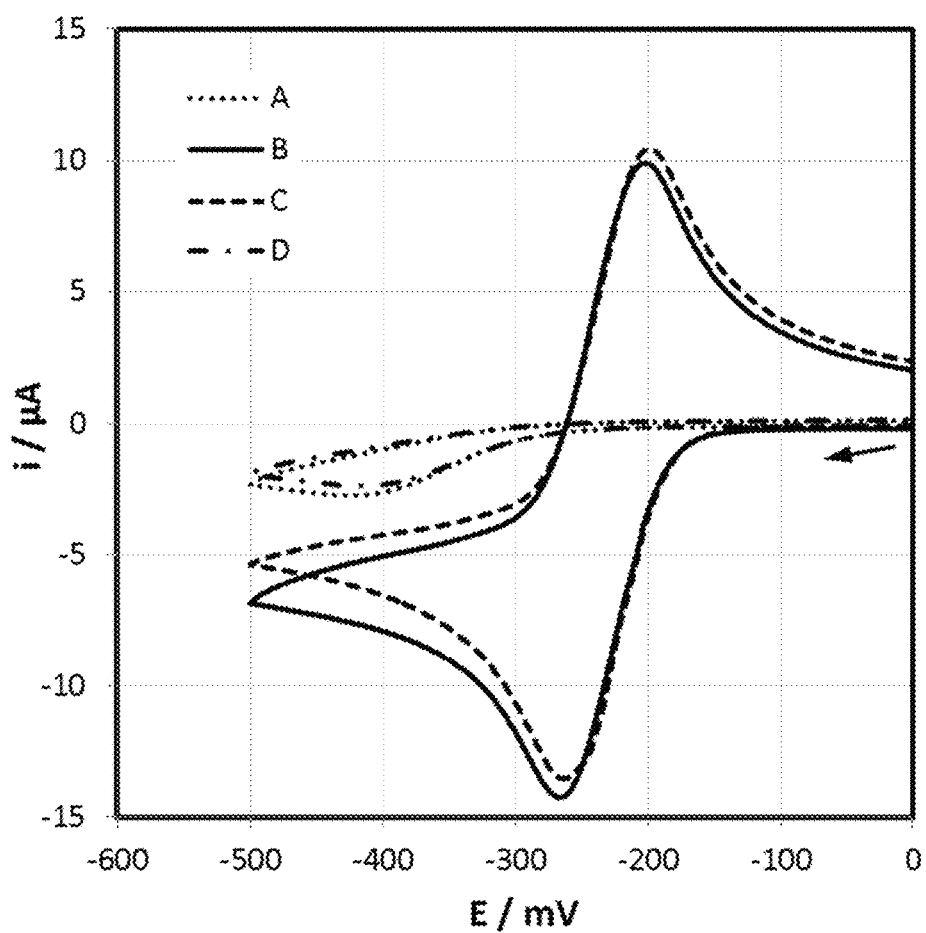

Kehrmann, F. and Masslenikoff, A., Über ein drittes Isomeres des Aposafranins., Chemische Berichte, 1911, pp. 2628-2631.
McMurray, English Excerpt, Organic Chemistry, 2012, p. 742, 8th Edition.
Slama, James T. and Simmons, Anne M., Carbanicotinamide Adenine Dinucleotide: Synthesis and Enzymological Properties of a Carbocyclic Analogue of Oxidized nicotinamide Adenine Dinucleotide, 1988, pp. 183-193, vol. 27.
Urleb, U. and Gobec, S., Product Class 16: Phenazines, Science of Synthesis, 2004, pp. 913-943, vol. 16.
Vázquez-Figueroa, Eduardo et al., Development of a Thermostable Glucose Dehydrogenase by a Structure-Guided Consensus Concept, ChemBioChem, 2007, pp. 2295-2301, vol. 8.
Yomo, Tetsuya et al., Synthesis and characterization of 1-substituted 5-alkylphenazine derivatives carrying functional groups, European Journal of Biochemistry, 1989, pp. 293-298, vol. 179.

PHENAZINIUM MEDIATORS

FIELD OF THE INVENTION

The present invention relates to a chemical compound or a salt or solvate thereof being a 1-amino-phenazine derivative and to uses thereof. The present invention further relates to a chemistry matrix and to a test element comprising the aforesaid chemical compound. Moreover, the present invention relates to a method for determining the amount of an analyte in a sample, comprising contacting said sample with a chemistry matrix according to the present invention, estimating the amount of electrons liberated or consumed by the chemistry matrix in the presence of said liquid sample, and thereby determining the amount of an analyte in a liquid sample.

RELATED ART

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods known to the skilled person make use of test elements comprising one or more test chemistries, which, in presence of the analyte to be detected, are capable of performing one or more detectable detection reactions, such as optically or electrochemically detectable detection reactions. With regard to these test chemistries and methods related thereto, reference may be made e.g. to J. Hoenes et al. (The Technology Behind Glucose Meters: Test Strips, Diabetes Technology & Therapeutics, Volume 10, Supplement 1, 2008, S-10 to S-26, to US 2009/0246808 A1, and to Habermüller et al. ((2000), Fresenius J Anal Chem 366:560). For electrochemical detection of glucose, a review is provided, e.g. in Heller & Feldman (2008), Chem. Rev. 108: 2482.

Particularly in electrochemical detection of analytes, phenazine derivatives have been proposed and evaluated as redox mediators in enzyme assays (Ghosh and Quayle (1979), Anal Biochem 99: 112; Hisada et al. (1981), J Appl Biochem 3:535; Yomo et al. (1989) Eur J Biochem 179:293) and in particular in enzyme assays depending on NAD as a cofactor, since azine mediators can be used with a low overpotential (Cooney et al. (2008), Energy Environ. Sci. 1: 320). However, reduced phenazine derivatives have a low solubility and, therefore, tend to form precipitates on the electrodes used in measurement, which are difficult to redissolve (Inzelt & Puskás (2004), Electrochimica Acta 49: 969). Moreover, the redox potential of phenazines described in the art lies within a range that permits reduction of said phenazines by compounds like, e.g. ascorbate, which is frequently administered to hospitalized patients, leading to systemic errors in, e.g. blood glucose determination of such patients (Heller & Feldman, loc. cit.).

Accordingly, there is a need in the art for phenazine derivatives having a good solubility even in the reduced state and being resistant to reduction by reducing agents used as pharmaceuticals, in particular ascorbate, but allowing fast reaction with reduced coenzyme.

Problem to be Solved

It is therefore an objective of the present invention to provide means and methods to comply with the aforementioned needs, avoiding at least in part the disadvantages of the prior art.

SUMMARY OF THE INVENTION

This problem is solved by a chemical compound or a salt or solvate thereof comprising the structure as disclosed herein, by a chemistry matrix comprising said chemical compound or salt or solvate thereof, by a test element comprising said chemical compound or salt or solvate thereof, and by the method for determining the amount of an analyte as disclosed herein. Typical embodiments, which might be realized in an isolated fashion or in any arbitrary combination are listed in the dependent claims and are described in this specification.

Accordingly, the present invention relates to a chemical compound or a salt or solvate thereof comprising the structure (I)

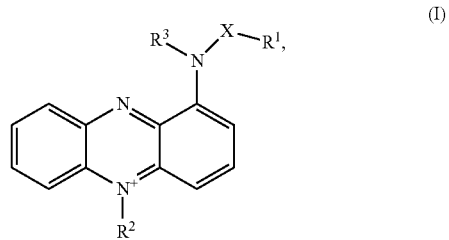

wherein
X is —C(=O)—, —C(=S)—, or —S(=O)$_2$—,
R$^1$ is an organic side chain comprising at least 2 C-atoms if X is C(=O), and at least 1 C-atom if X is C(=S) or S(=O)$_2$,
R$^2$ is an organic side chain comprising at least 2 C-atoms,
R$^3$ is H or an organic side chain, and
wherein at least one of R$^1$, R$^2$ and R$^3$ is a hydrophilic side chain.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "typically", "more typically", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

As used herein, the terms "chemical compound", "salt", and "solvate" are used in their usual meaning known to the skilled chemist. If the net charge of a compound according to the present invention is positive, typical counterions are trifluoromethanesulfonate (triflate), sulfate, alkyl sulfonate, tosylate, phosphate, tetrafluoroborate, hexafluorophosphate, trifluoracetate, perchlorate, chloride or nitrate ions. If the net charge of a compound according to the present invention is negative, typical counterions are lithium, sodium, and/or potassium ions, or tetramethlyammonium ions. Typically, the net charge of a compound according to the present invention is the net charge of the compound in aqueous solution under standard conditions as specified elsewhere herein.

The term "side chain" is understood by the skilled person and relates to an atom or chemical group attached covalently to the core part of a chemical compound as described herein, said core part also being referred to as "main chain" or "backbone". Typically, the side chain is an organic side chain as described herein below. The term "substituted" side chain relates to a side chain substituted at one or more positions, typically, at 1, 2, or 3 positions, wherein substituents may be attached at any available atom to produce a stable chemical compound. It is understood by the skilled person that the term "optionally substituted" side chain relates to an unsubstituted or to a substituted side chain.

The term "organic side chain", as used herein, relates to any, optionally substituted, side chain comprising at least one carbon atom. Typically, the organic side chain is an, optionally substituted, alkyl, alkenyl, alkinyl, aryl, aralkyl, cycloalkyl, heterocycloalkyl, or heteroaryl side chain. Typically, a substituted organic side chain is an organic side chain substituted with at least one substituent independently selected from —COO$^-$, =O, —OH, —CN, halogen, —NH$_2$, —NH(alkyl), —N(alkyl)$_2$, —N(alkyl)$_3^+$, —NH(aryl), N(aryl)$_2$, —NO$_2$, —O(alkyl), —O—(CH$_2$)$_n$—OH, —O—(CH$_2$)n-O(alkyl), —O(aralkyl), —O(aryl), —OPO$_3^{2-}$, —PO$_3^{2-}$, —OSO$_3^-$ and —SO$_3^-$. Typically, the alkyl, aryl, and aralkyl groups of the substituents are not further substituted by groups comprising alkyl, alkenyl, alkinyl, aryl, aralkyl, heterocycloalkyl, or heteroaryl groups. More typically, the alkyl, aryl, and aralkyl groups of the substituents are not further substituted.

The term "alkyl", as used herein, relates to a straight or branched chain, saturated hydrocarbon group, linked to the main chain by a covalent bond to at least one of its at least one carbon atoms. Typical alkyl groups are straight chain alkyls, e.g., typically, methyl, ethyl, propyl, butyl, pentyl, hexyl, heptyl, octyl, nonyl, decyl, undecyl, dodecyl, or branched chain alkyl groups, e.g., typically, —CH(CH$_3$)$_2$, —CH(CH$_2$CH$_3$)$_2$, —C(CH$_3$)$_3$, —C(CH$_2$CH$_3$)$_3$, —CH(CH$_3$)(CH$_2$CH$_3$), —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH3)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, or —CH(CH$_3$)CH(CH$_3$)CH(CH$_3$)$_2$. Accordingly, alkyl groups include primary alkyl groups, secondary alkyl groups, and tertiary alkyl groups. The term "cycloalkyl" relates to a circularly closed, hydrocarbon group, typically with 3 to 12 carbon atoms. Typical cycloalkyls are cyclopropyl, cyclobutyl, cyclopentyl, cyclohexyl, cycloheptyl, and cyclooctyl.

The term "alkenyl" side chain relates to a side chain comprising at least one C=C double bond and linked to the main chain by a covalent bond to at least one of its at least two carbon atoms. Accordingly, the term "alkinyl" side chain relates to a side chain comprising at least one C≡C triple bond linked to the main chain by a covalent bond to at least one of its at least two carbon atoms.

The term "cycloalkenyl" relates to a circularly closed hydrocarbon group, typically with 5 to 12 carbon atoms, comprising at least one C=C double bond and linked to the main chain by a covalent bond to at least one of its at least two carbon atoms. The term "cycloalkinyl" relates to a circularly closed hydrocarbon group, typically with 8 to 12 carbon atoms, comprising at least one C≡C triple bond and linked to the main chain by a covalent bond to at least one of its at least two carbon atoms.

As used herein, the term "alkoxy" side chain relates to an —O-alkyl side chain, typically having the indicated number of carbon atoms. Typically, the alkoxy side chain is —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, or —O-neohexyl.

The term "aryl", as used herein, relates to an aromatic ring or ring system having 6 to 14 carbon atoms, typically comprising one, two, or three aromatic rings. Typical aryl side chains are phenyl, naphthyl, anthracenyl, and phenanthrenyl. The term "ring", in the context of the chemical compounds of the present invention, is understood by the skilled person; accordingly, the term "ring system" relates to a chemical structure comprising at least two rings sharing at least one covalent bond. Thus, typically, "aryl" also includes aromatic ring systems fused with a cycloalkyl and/or a heterocycloalkyl ring.

As used herein, the term "aralkyl" relates to an alkyl side chain, wherein at least one hydrogen is replaced by an aryl side chain. Typically, aralkyl is benzyl or phenethyl.

The term "heterocycloalkyl", as used herein, relates to a saturated or partially unsaturated ring or ring system having 5 to 14 ring atoms, typically 5 to 7 ring atoms, wherein at least one ring atom is a heteroatom selected from the group consisting of N, O, and S, said ring or ring system being linked to the main chain by a covalent bond to a C or N atom of said ring or ring system. Typically, heterocycloalkyl is azepinyl, dihydrofuryl, dihydropyranyl, imidazolidinyl, imidazolinyl, isothiazolidinyl, isoxazolidinyl, morpholinyl, oxazolidinyl, piperazinyl, piperidinyl, pyrazolidinyl, pyrrolidinyl, tetrahydrofuryl, tetrahydropyranyl, thiadiazolylidinyl, thiazolidinyl, or thiomorpholinyl.

As used herein, the term "heteroaryl" relates to an aromatic ring or ring system having 5 to 14 ring atoms, typically 5 to 7 ring atoms, wherein at least one ring atom is a heteroatom selected from the group consisting of N, O, and S, said ring or ring system being linked to the main chain by a covalent bond to a C or N atom of said ring or ring system. Typically, up to 4, more typically up to 3, most typically up to 2 ring atoms per ring are heteroatoms independently selected from the group of heteroatoms consisting of N, O, and S. Typically, heteroaryl is pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, or indolyl.

The term "hydrophilic" is known to the skilled person and relates to the property of a chemical compound or of a portion of a chemical compound of having a tendency to dissolve in, mix with, or be wetted by a polar solvent, in particular water. As used in the context of the side chains of the present invention, the term "hydrophilic side chain", typically, relates to a side chain as specified herein, having an octanol/water coefficient (log $K_{OW}$) of ≤2, more typically ≤1.5, still more typically ≤1, or, most typically, ≤0.8, under standard conditions of 25° C., $10^8$ Pa, and pH=7. In the context of the present specification, the log $K_{OW}$ value of a side chain $R^x$ (with x=1, 2, or 3) is assumed to be identical to the log $K_{OW}$ value of the chemical compound of the formula H—$R^x$. The skilled person knows how to determine the log $K_{OW}$ value of a chemical compound. Typically, the hydrophilic side chain comprises at least one hydrophilic functional group selected from the group consisting of —C(=$Y^1$)—OH, —C(OH)$R^{11}R^{12}$, —C(=$Y^1$)—$R^{11}$, —C(=$Y^1$)—$Y^2$—$R^{11}$, —$Y^1$—$R^{11}$, —$NH_2$, —$NHR^{11}$, —$NMe^{3+}$, —NH—C(=$Y^1$)—$R^{11}$, —S(O)$R^{11}$, —$SO_2R^{11}$, —$SO_2$—OH—, and —P(O)($OR^{11}$)($OR^{12}$)—O—P(O)($OR^{11}$)($OR^{12}$)— with $Y^1$ and $Y^2$ being independently selected from O or S and with $R^{11}$ and $R^{12}$ being, independently of each other, elected from the group consisting of H and, unsubstituted or substituted, alkyl and aryl. More typically, the hydrophilic side chain comprises at least one hydrophilic functional group selected from C(=O)— and —C(=O)—OH. Most typically, a hydrophilic side chain is a side chain comprising at least one chemical group bearing a charge, typically a negative charge, under the aforesaid standard conditions.

In the context of the structural formulas of the present specification, side chain $R^1$ is an organic side chain comprising at least 2 C-atoms if X is C(=O), and at least 1 C-atom if X is C(=S) or S(=O)$_2$. Typically, side chain $R^1$ is an, optionally substituted, organic side chain, typically alkyl, with a contiguous chain of 3 to 20 C-atoms covalently bound to the C or S atom of the group X of formula (I) or (II). More typically, side chain $R^1$ is alkyl with a contiguous chain of 3 to 8 C-atoms covalently bound to the C or S atom of the group X of formula (I) or (II), comprising at least one substituent independently selected from OH, $OPO_3^{2-}$, $PO_3^{2-}$, $SO_3^-$, and $COO^-$. Typically, side chain $R^1$ is a linker, typically an alkyl linker, more typically an unbranched alkyl linker, covalently connecting one molecule of the chemical compound to a second molecule of the chemical compound, i.e. typically, the chemical compound is a dimer, wherein the two molecules are connected via a linker. Typical dimers according to the present invention are shown herein in the examples, in particular the compounds having a structure according to one of formulas (XVII), (XVIII), (XIX), or (XX). Typically, said linker has at least 3 C-atoms, more typically 3 to 20 C-atoms. Typically, the chain of carbon atoms of $R^1$ is interrupted by one or more —NHCO— and/or —O— entities wherein two —NHCO— entities are separated by a minimum of one C atom and the —O— entities by a minimum of two C atoms; e.g., more typically, said linker comprises a poly-glycine and/or a poly-ethyleneglycol chain. Optionally, the side chain is additionally substituted with —OH groups, wherein the —OH group is never bound to a carbon atom which is linked to an optional O— atom of the chain.

As used in the context of formula (I) and (II), X is C(=Y) with Y being O or S, or X is S(=O)$_2$. Typically, X is C(=O). Accordingly, —X—$R^1$ of formula (I) or (II), typically, is fumaryl, glutaryl, adipyl, or, most typically, succinyl.

In the context of the structural formulas of the present specification, side chain $R^2$ is an organic side chain comprising at least 2 C-atoms. Typically, side chain $R^2$ is, optionally substituted, alkyl, aryl, or aralkyl, typical substituents for the aforesaid organic side chains in the context of $R^2$ being —OH, $OPO_3^{2-}$, $PO_3^{2-}$, $SO_3^-$, and, most typical, $COO^-$. More typically, $R^2$ has the structure —$(CH_2)_n$—$CH_3$ with n being in the range of from 0 to 6, still more typically with n being 0, 1 or 2; most typically, $R^2$ is ethyl. Typically, the chain of carbon atoms of $R^2$ is interrupted by one or more —NHCO— and/or —O— entities wherein two —NHCO— entities are separated by a minimum of one C atom and the —O— entities by a minimum of two C atoms; e.g., more typically, said linker comprises a poly-glycine and/or a poly-ethyleneglycol chain. Optionally, the side chain is additionally substituted with —OH groups, wherein the —OH group is never bound to a carbon atom which is linked to an optional O— atom of the chain. In another typical embodiment, $R^2$ is, optionally substituted, aryl; more typically $R^2$ is phenyl.

In the context of the structural formulas of the present specification, side chain $R^3$ is a side chain as described herein above. Typically, $R^3$ is H.

In the chemical compound of the present invention, least one of $R^1$, $R^2$, and $R^3$, typically at least one of $R^1$ and $R^2$ is a hydrophilic side chain as specified herein above. Typically, at least two of $R^1$, $R^2$, and $R^3$ are hydrophilic side chains, more typically at least $R^1$ and $R^2$ are hydrophilic side chains or $R^2$ and $R^3$ are hydrophilic side chains. Typically, side chains $R^1$, $R^2$, and $R^3$ are selected such that the solubility of the compound according to the present invention is at least 15 mmol/L, more typically at least 25 mmol/L, most typically at least 50 mmol/L, wherein solubility, typically, is solubility in water determined under standard conditions, more typically under standard conditions as specified elsewhere herein.

Typically, the chemical compound or salt or solvate thereof has the structure (II)

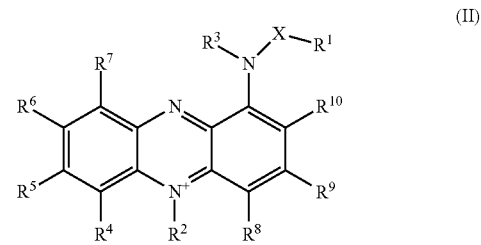

(II)

wherein $R^4$, $R^5$, $R^6$, $R^7$, $R^8$, $R^9$, and $R^{10}$ are, independently of each other, selected from the group consisting of H; substituted or unsubstituted alkyl, cycloalkyl, alkenyl, cycloalkenyl, alkinyl, aryl, heterocycloalkyl, heteroaryl, halogen; —$NO_2$, —$SO_3^-$—CN, —CH=CH—COOH, and —$Y^3$—$R^{13}$ with $Y^3$ being —O—, —C(=O)— or —N($R^{14}$)—, with $R^{13}$ and $R^{14}$ being, independently of each other, selected from the group consisting of unsubstituted or substituted, alkyl and aryl. Typically, $R^5$ and/or $R^9$ are alkyl or cycloalkyl. More typically, $R^5$ and/or $R^9$ are —H, methyl, —F, —Cl, —C(=O)—, —$NO_2$, —$SO_3^-$—CN, or —CH=CH—COOH. Most typically, $R^4$, $R^5$, $R^6$, $R^7$, $R^8$, $R^9$ and $R^{10}$ are —H.

More typically, the chemical compound or salt or solvate thereof has the structure (II), wherein $R^3$, $R^4$, $R^6$, $R^7$, $R^8$, and $R^{10}$ are H;

X is C=O; and $R^1$ and/or $R^2$ are hydrophilic alkyl, aryl or aralkyl side chains, typically compromising a negatively charged group, more typically COO$^-$, SO$_3^-$, —OPO$_3^{2-}$, or PO$_3^{2-}$.

Still more typically, the chemical compound or salt or solvate thereof has the structure of a formula selected from the formulas as shown in Table 1.

TABLE 1 typical chemical compounds of the present invention.

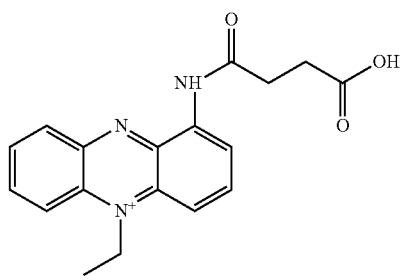 [SMILES: CC[n+]1c2ccccc2nc2c(NC(=O)CCC(=O)O)cccc21]
(III)

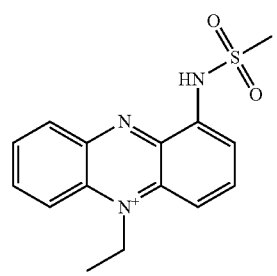 [SMILES: CC[n+]1c2ccccc2nc2c(NS(C)(=O)=O)cccc21]
(IV)

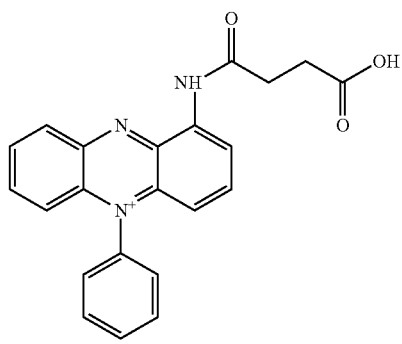 [SMILES: O=C(O)CCC(=O)Nc1cccc2c1nc1ccccc1[n+]2-c1ccccc1]
(V)

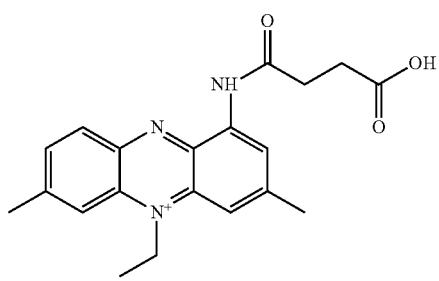 [SMILES: CC[n+]1c2cc(C)ccc2nc2c(NC(=O)CCC(=O)O)cc(C)cc21]
(VI)

TABLE 1-continued typical chemical compounds of the present invention.

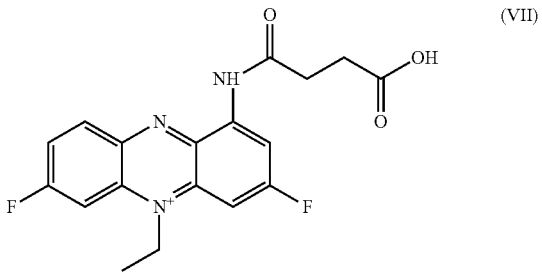
(VII)

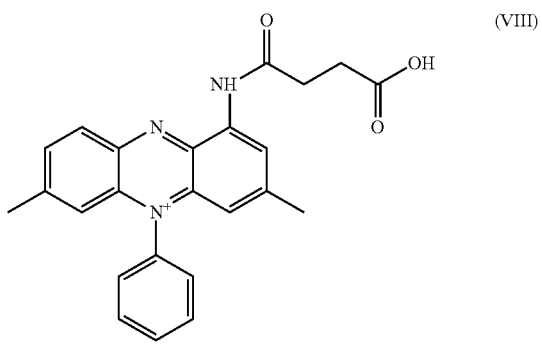
(VIII)

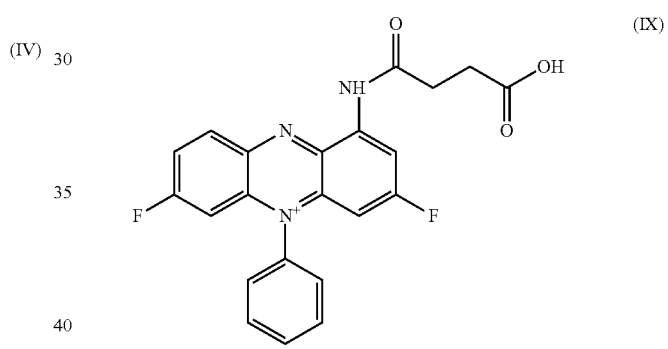
(IX)

Most typically, the chemical compound or salt or solvate thereof has the structure of formula (III).

Advantageously, it was found in the work underlying the present invention that addition of bulky side chains to 1-amino-phenazine compounds reduces the tendency of said compounds to undergo redox reactions with reducing agents potentially present in biological samples, like, e.g., ascorbate, and that said effect is most pronounced when said bulky side chains are introduced into at least one of the positions labeled $R^1$, $R^2$, and $R^3$ in formulas (I) and (II). Moreover, it was found that solubility of the compounds, in particular their tendency to precipitate upon reduction, can be improved by including at least one hydrophilic side chain in at least one of the positions labeled $R^1$, $R^2$, and $R^3$ in formulas (I) and (II). Moreover, it was found that compounds having one of the aforesaid structures are stable for more than half a year when included in a chemistry matrix. All of the aforesaid effects were most pronounced when bulky and negatively charged side chains were used. Without wishing to be bound by theory, the negatively charged group of the side chain may also interact with the positively charged phenazinium ring, which may result in stabilization of the oxidized form.

The definitions made above apply mutatis mutandis to the following. Additional definitions and explanations made further below also apply for all embodiments described in this specification mutatis mutandis.

The present invention further relates to a chemistry matrix comprising a chemical compound of the present invention.

The term "chemistry matrix" is known to the skilled person. Typically, the chemistry matrix of the present invention, in addition to the chemical compound of the present invention, comprises an oxidoreductase and a redox cofactor as described herein below. It is understood by the skilled person that the composition may comprise additional components, e.g., typically, buffer components (e.g., of phosphate buffered saline, Tris buffer, citrate buffer, glycerine phosphate buffer, or Good's buffer) or other salts, detergents, or the like, including the components as specified herein below.

A chemistry matrix according to the present invention can be provided, typically, by dissolving the components of the composition of the present invention first in a solvent or mixture of solvents. More typically, said solvent or mixture of solvents is subsequently removed by a suitable treatment such that the remaining composition is essentially free of the said solvent or solvent mixture. Suitable treatments to be typically envisaged by the present invention include heat treatment, evaporation techniques, freeze drying and the like. Typically, the envisaged treatment is heat treatment and, in particular, heat treatment under the following conditions: heat treatment at about 60° C. or more for approximately 20 to 45 minutes or at about 95° C. for approximately 1 to 2 minutes with heat circulation; thickness of the chemistry matrix of 20 to 200 micrometers or less; at a pressure of 1 bar or 0.1 bar. Moreover, it will be understood that in order to keep the chemistry matrix under dry conditions, storage is, typically, carried out in the presence of a drying agent, i.e., a desiccant. Suitable drying agents, typically, encompass silica gel, zeolites, calcium carbonate or magnesium sulfate.

The term "oxidoreductase" as used herein refers to a polypeptide which is capable of catalyzing the, typically specific, oxidation or reduction of a substrate by transferring hydrides ($H^-$) as redox equivalents to or from a redox cofactor as referred to herein elsewhere. Typically, the oxidoreductase is a dehydrogenase, i.e. a polypeptide which is capable of catalyzing the oxidation of a substrate by transferring hydrides ($H^-$) as redox equivalents to an acceptor molecule, typically, to a redox cofactor as referred to herein elsewhere. Dehydrogenases envisaged by the present invention are, typically, those which depend on a redox cofactor (or sometimes referred to as co-enzyme) such as pyrrolo quinoline quinone (PQQ) or a derivative thereof, nicotinamide-adenine-dinucleotide (NAD) or a derivative thereof, or a flavine cofactor, such as flavin-adenine-dinucleotide (FAD) or flavine mononucleotide (FMN), or a derivative thereof. Typical dehydrogenases are, in particular, lactate dehydrogenase (EC number 1.1.1.27 or 1.1.1.28), glucose dehydrogenases (see below), alcohol dehydrogenase (EC number 1.1.1.1 or 1.1.1.2), L-amino acid dehydrogenase (EC number 1.4.1.5), glycerol dehydrogenase (EC number 1.1.1.6), malate dehydrogenase (EC number 1.1.1.37), 3-hydroxybutyrate dehydrogenase (EC number 1.1.1.30), or sorbitol dehydrogenase (EC number 1.1.1.14).

More typically, said oxidoreductase is a glucose dehydrogenase. Most typically, said glucose dehydrogenase is selected from the group consisting of: glucose dehydrogenase (EC number 1.1.1.47), quinoprotein glucose dehydrogenase (EC number 1.1.5.2), in particular, pyrrolo quinoline quinone (PQQ)-dependent glucose dehydrogenase (EC number 1.1.5.2), glucose-6-phospate dehydrogenase (EC number 1.1.1.49), nicotinamide adenine dinucleotide (NAD)-dependent glucose dehydrogenase (EC number 1.1.1.119) and flavin adenine dinucleotide (FAD)-dependent glucose dehydrogenase (EC number 1.1.99.10) or enzymatically active mutants thereof.

Enzymatically active mutants of the aforementioned enzymes can be obtained by substituting, adding or deleting one or more amino acids from the amino acid sequences reported for the aforementioned wild type enzymes in the prior art as recited before. Typical mutants are the mutants of the PQQ-dependent glucose dehydrogenase having an improved substrate specificity compared to their wild type counterparts as disclosed in U.S. Pat. No. 7,132,270 or U.S. Pat. No. 7,547,535. Both documents are herewith incorporated by reference with respect to the mutants. Further mutants are those disclosed in Baik et al (Baik 2005, Appl Environ Microbiol 71: 3285), Vasquez-Figuera et al. (Vasquez-Figuera 2007, Chem BioChem 8: 2295), and WO 2005/045016.

Typical in accordance with the present invention is a glucose dehydrogenase (E.C. 1.1.1.47) mutant disclosed in WO2009/103540A1 (p.21) or EP1660648, having a mutation at least at amino acid positions 96, 170 and/or 252, herewith incorporated by reference. Typical mutations envisaged at theses amino acid positions are substitutions of Glu96Gly, Glu170Arg or Lys and/or Lys252Leu, the combination Glu170Lys/Lys252Leu being more typical. Most typically, said mutations are mutations Glu170Arg and Gln252Leu in glucose dehydrogenase from *Bacillus subtilis*.

The term "redox cofactor", as used herein, relates to a redox-active flavine, nicotinamide or pyrrolo quinoline quinone (PQQ) coenzyme. The skilled person knows how to select one of the aforesaid coenzymes appropriately, depending on the oxidoreductase selected. Typically, the flavine, nicotinamide or PQQ coenzyme is flavine adenine dinucleotide (FAD), flavine mononucleotide (FMN), or PQQ, or a derivative of one of the aforesaid compounds. More typically, the flavine, nicotinamide or PQQ coenzyme is nicotinamide adenine dinucleotide ($NAD^+$), nicotinamide adenine dinucleotide phosphate ($NADP^+$), or a derivative thereof. Typical $NAD^+$ or $NADP^+$ derivatives are stabilized $NAD^+$ or $NADP^+$ derivatives, i.e. typically, carbacyclic derivatives, including, more typically, carba$NAD^+$ or carba$NADP^+$, as disclosed, e.g. typically, in Slama (Biochemistry 27: 183 (1988)), Hutchinson et al. (Chem. Comm. 24: 2765 (1996)), U.S. Pat. No. 5,801,006, WO98/33936, WO01/49247 and WO2007/012494. Most typically, the redox cofactor is $NAD^+$, $NADP^+$, carba$NAD^+$, or carba$NADP^+$.

The term "redox equivalents" as used herein relates to the concept commonly used in redox chemistry well known to the skilled person. Typically, the term relates to electrons which are transferred from a substrate of the oxidoreductase to the redox cofactor, and/or from said redox cofactor to a redox mediator, and/or from said redox mediator to and indicator compound and/or to an electrode.

In a typical embodiment of the chemistry matrix of the present invention, said composition further comprises at least one detergent, swelling agent, film-forming agent, and/or solid particle. Suitable stabilizers, detergents, swelling agents, film forming agents, oxidizing agents, and/or solid particles to be used in the composition of the invention are known to the skilled artisan. Typically, the said at least one detergent is selected from the group consisting of: Sodium-N-methyl-N-oleoyltaurat, N-octanoyl-N-methyl-glucamid, Mega 8 (N-methyl-N-octanoylglucamide), dioctylsodium sulfosuccinate (DONS), Rhodapex® (typically CO-433 or CO-436). Typically, said at least one swelling agent is selected from the group consisting of: methyl vinyl ether maleic acid anhydride copolymer, xanthan gum and methyl vinyl ether maleic acid copolymer. Typically, said at least one film-forming agent is selected from the group consisting of: polyvinylpropionate dispersions, Polyvinyl esters, polyvinyl acetates, polyacrylic esters, polymethacrylic acid, polyvinyl amides, polyamides, polystyrene and mixed polymerisates are also suitable such as of butadiene, styrene or maleic acid ester. Typically, said at least one solid particle is selected from the group consisting of: silica particles, in particular, silicon dioxide, sodium silicates or aluminium silicates, kieselgur, metal oxides, in particular, titan oxide and/or aluminium oxide, synthetic oxide materials, in particular, nanoparticles of oxide materials such as nanoparticles of silicon dioxide, aluminium oxide, or titan oxide, Kaolin, powder glass, amorphous silica, calcium sulfate, and barium sulfate.

Moreover, the present invention relates to a test element comprising the chemical compound of the present invention and/or the chemistry matrix of the present invention.

The term "test element", as used herein, relates to a unit comprising a test chemistry composition, typically a dry test chemistry composition, on a solid support. Typically, the test chemistry composition is comprised in a test field as described herein below. Also typically, the test element further comprises a capillary element, adapted for taking up and/or transporting a liquid by capillary action, typically to a test field. Typically, the test element is selected from an optical test element and an electrochemical test element. The test element may further optionally comprise at least one puncture element, such as a lancing element, which, typically, may be mounted movably with regard to the test field, in order to perform a puncture motion, a sampling motion or a lancing motion, thereby generating an incision in a skin surface. Typically, the test field remains in a fixed position during the puncture, sampling or lancing motion, wherein a sample of a body fluid is transferred onto the test field, such as by a capillary action and/or by pressing the puncture element or a part thereof onto the test field after the puncture, sampling or lancing motion. Typically, the test element is a test strip, a test tape, or a test disc.

The term "test field" relates to a continuous or discontinuous amount of test chemistry composition, which, typically, is held by at least one carrier, such as by at least one carrier film. Thus, the test chemistry may form or may be comprised in one or more films or layers of the test field, and/or the test field may comprise a layer setup having one or more layers, wherein at least one of the layers comprises the test chemistry. Thus, the test field may comprise a layer setup disposed on a carrier, wherein a sample of a body fluid may be applied to the layer setup from at least one application side, such as from an edge of the test field and/or from an application surface of the test field. Typically, the test field has a multilayer setup, the multilayer setup comprising at least one detection layer having the at least one test material and further comprising at least one separation layer adapted for separating off at least one particulate component contained in the body fluid, wherein the separation layer is located between the detection layer and the capillary element. It is understood by the skilled person that all layers present optionally between the body fluid and the test field are selected as to allow passage of at least the analyte.

Typically, the test element is an optical test element, i.e. a test element adapted to change at least one optical property in the presence of the analyte. More typically, at least one chemistry matrix comprised in the test element performs at least one optically detectable detection reaction in the presence of the analyte. Even more typically, the detection reaction is a redox reaction. Most typically, the detection reaction produces redox equivalents and/or electrons as intermediates and/or products. Typically, the optically detectable signal produced by the detection reaction is proportional to the amount and/or to the concentration of the analyte in the sample.

Typically, the test element adapted to change at least one optical property in the presence of an analyte, typically the chemistry matrix comprised in said test element, comprises at least one indicator reagent changing at least one optical property in the presence of redox equivalents in addition to the components detailed above. The term "indicator reagent", as used herein, typically, relates to a compound changing at least one optical property dependent on, typically proportional to, the activity of the enzyme of the present invention. Typically, the indicator reagent is an optical indicator substance, which performs at least one optically detectable property change when at least one of the enzymes or when the enzyme comprised in the chemistry matrix reacts with the analyte. Thus, the at least one indicator reagent typically comprises one or more dyes performing a change in an optical property indicative of the enzymatic reaction of the at least one enzyme and the analyte.

The term "optical property", as used herein, relates to a property which can be detected by an optical instrument. Specifically, the optical property may be or may comprise at least one property selected from the group consisting of: a reflection property, a transmission property, an emission property, a scattering property, a fluorescence property, a phosphorescence property, a diffraction property, and a polarization property. Typically, an optical property as referred to herein refers to a property of the indicator reagent which can be optically detected such as light absorption, light emission, light remission, or properties associated therewith. It will be understood that such a change of at least one optical property as used herein encompasses the detection of the presence of a property which was not detectable before, the detection of the absence of a property which has been detected before, and the detection of quantitative changes of a property, i.e., the detection of the change of the signal strength which correlates to the extent of the change of the at least one optical property. Typical optical properties envisaged by the present invention are color, fluorescence, luminescence, or refractometry. Dependent on the desired optical property to be detected in the chemistry matrix, the skilled person is in a position to select without further ado a suitable indicator reagent. Methods of converting the optical property as defined above into a physical signal which can be read as a measurement value are well known in the art and are described, e.g., in EP 0 821 234, EP 0 974 303, and US 2005/0023152.

The optical property of the indicator reagent, according to the present invention, changes dependent on the activity of the enzyme of the present invention. Thus, typically, the change of the optical property only occurs if the enzyme catalyzes the detection reaction. More typically, the change of optical property is proportional to the number of catalytic cycles undergone by the enzyme present in the chemistry matrix. Thus, most typically, the change of optical property is proportional to the number of analyte molecules converted by the enzyme.

More typically, the test element is an electrochemical test element. Accordingly, the test element, typically, comprises at least two electrodes contacting, directly or indirectly, the chemistry matrix, as specified herein below. Suitable electrodes, electrode setups, and modes of operation are known to the skilled person and are described, e.g. in WO 2007/071562 A1, WO 2014/001382 A1, US 2005/0023152 and references cited therein. Moreover, it is envisaged by the present invention that the chemistry matrix includes one or more chemical reagents for reacting with the analyte to produce an electrochemical signal that represents the presence of the analyte in the sample fluid. Typically, the one or more chemical reagents for reacting with the analyte to produce an electrochemical signal that represents the presence of the analyte in the sample fluid comprises a chemical compound of the present invention. More typically, the chemical reagents for reacting with the analyte to produce an electrochemical signal, in addition to a chemical compound of the present invention, further comprise at least one oxidoreductase as described herein above. Most typically, the chemical reagents for reacting with the analyte to produce an electrochemical signal, in addition to a chemical compound of the present invention and at least one oxidoreductase, further comprise at least one redox cofactor as described herein above. Typically, electrochemical properties include amperometric or coulometric responses indicative of the concentration of the analyte. See, for example, U.S. Pat. Nos. 5,108,564, 4,919,770 and 6,054,039.

Typically, the electrochemical test element comprises at least two electrodes contacting the chemistry matrix comprised in said test element, or contacting means conductively connected to said test chemistry. Typically, the means conductively connected to a chemistry matrix is a layer of a test strip connected to a chemistry matrix to enable diffusion of a redox cofactor and/or of a redox mediator through said layer. More typically, the means conductively connected to a chemistry matrix is a layer of a test strip at least partially overlaying and/or underlaying said chemistry matrix to enable diffusion of a redox cofactor and/or of a redox mediator through said layer.

The electrochemical property, according to the present invention, changes dependent on the activity of the oxidoreductase of the present invention. Thus, typically, the change of the electrochemical property only occurs if the oxidoreductase catalyzes the detection reaction. More typically, the change of optical property is proportional to the number of catalytic cycles undergone by the oxidoreductase present in the chemistry matrix. Thus, most typically, the change of optical property is proportional to the number of analyte molecules converted by the oxidoreductase.

The present invention also relates to a device for determining the amount of an analyte in a liquid sample, comprising a chemical compound of the present invention and/or a test element according to the present invention. Typically, the device further comprises an optical and/or an electrochemical sensor.

Further, the present invention relates to the use of a chemical compound according to the present invention in an analytical or diagnostic test.

Typically, the analytical or diagnostic test comprises qualitative and/or quantitative determination of any biological or chemical analyte detectable by optical or electrochemical means. Typically, the analyte is comprised in a test sample of a subject, more typically a test sample of a body fluid. More typically, the analytical or diagnostic test comprises determining glucose concentration in a test sample. Most typically, the analytical or diagnostic test comprises determining glucose concentration in a test sample from a subject suffering from diabetes or suspected to suffer from diabetes. Also typically, the analytical or diagnostic test is a test for monitoring blood glucose concentrations, typically in a subject suffering from diabetes or suspected to suffer from diabetes. The analytical or diagnostic test, typically, is an in vitro test.

The term "analyte", as used herein, relates to a chemical compound present in a body fluid. Typically, the analyte is a small molecule, i.e., typically, the analyte is not a biological macromolecule. More typically, the analyte is an organic molecule, most typically an organic molecule capable of undergoing a redox reaction in the presence of the test chemistry according to the present invention. Typically, the analyte is a molecule of the subject's metabolism. Also typically, the analyte is a low molecular weight chemical compound, more typically a chemical compound with a molecular mass of less than 1000 u (1000 Da; $1.66 \times 10^{-24}$ kg). More typically, the analyte is selected from the list consisting of malate, ethanol, ascorbic acid, cholesterol, glycerol, urea, 3-hydroxybutyrate, lactate, pyruvate, triglycerides, ketones, liver parameters, creatinine, HDL, and the like; more typically, the analyte is blood glucose.

As used herein, the term "subject" relates to a vertebrate. Typically, the subject is a mammal, more typically, a mouse, rat, cat, dog, hamster, guinea pig, sheep, goat, pig, cattle, or horse. Still more typically, the subject is a primate. Most typically, the subject is a human. Typically, the subject is afflicted or suspected to be afflicted with a disease or condition associated with a measurable deviation from normal of at least one analyte. More typically, the subject is afflicted with diabetes. Typically, the subject receives a, typically systemic, treatment with a reducing agent, typically a treatment with ascorbate (vitamin C).

As used herein, the term "body fluid" relates to all bodily fluids of a subject known to comprise or suspected to comprise the analyte of the present invention, including blood, plasma, serum, lacrimal fluid, urine, lymph, cerebrospinal fluid, bile, stool, sweat, interstitial fluid, and saliva. Typically, the body fluid is blood, plasma, or serum.

The term "test sample" is understood by the skilled person and relates to any suitably sized subportion of a tissue or, typically, of a bodily fluid of a subject. Body fluid test samples can be obtained by well known techniques including, e.g., venous or arterial puncture, epidermal puncture, and the like.

The term "diabetes" or "diabetes mellitus", as used herein, refers to disease conditions in which the glucose metabolism is impaired. Said impairment results in hyperglycemia. According to the World Health Organization (WHO), diabetes can be subdivided into four classes. Type 1 diabetes is caused by a lack of insulin. Insulin is produced by the so called pancreatic islet cells. Said cells may be destroyed by an autoimmune reaction in Type 1 diabetes (Type 1a). Moreover, Type 1 diabetes also encompasses an idiopathic variant (Type 1b). Type 2 diabetes is caused by an insulin resistance. Type 3 diabetes, according to the current classification, comprises all other specific types of diabetes mellitus. For example, the beta cells may have genetic defects affecting insulin production, insulin resistance may be caused genetically or the pancreas as such may be destroyed or impaired. Moreover, hormone deregulation or drugs may also cause Type 3 diabetes. Type 4 diabetes may occur during pregnancy. Typically, diabetes as used herein refers to diabetes Type 1 or, more typically, Type 2. According to the German Society for Diabetes, diabetes is diagnosed either by a plasma glucose level being higher than 110 mg/dl in the fasting state or being higher than 220 mg/dl postprandial. Further typical diagnostic techniques for diagnosing diabetes, which may be used in conjunction with or in addition to the analytical or diagnostic tests of the present invention are well known in the art and are described in standard text books of medicine, such as Stedman or Pschyrembl.

It is understood by the skilled person that in diabetes, blood glucose levels have to be checked on a regular basis, in order to avoid and/or take countermeasures against hyperglycemia, e.g. after meals, or to avoid and/or take countermeasures against hypoglycemia, e.g. after administration of insulin. Accordingly, the present invention relates also to a chemical compound of the present invention for determining blood glucose levels, more typically, for use in diagnosing hyperglycemia, hypoglycemia, or normal glucose levels.

The present invention also relates to the use of a chemical compound according to present invention for the manufacture of a chemistry matrix according to the present invention or for the manufacture of a device according to the present invention.

Moreover, the present invention relates to a method for determining the amount of an analyte in a sample, comprising:
a) contacting said sample with a chemistry matrix according to the present invention,
b) estimating the amount of redox equivalents liberated or consumed by the chemistry matrix in the presence of said sample, and
c) thereby determining the amount of an analyte in a sample.

The method for determining the amount of an analyte, typically, is an in vitro method. Moreover, it may comprise steps in addition to those explicitly mentioned above. For example, further steps may relate, e.g., to processing and/or conditioning of a sample for step a), or applying voltage to and/or measuring current within said chemistry matrix in step b). Moreover, one or more of said steps may be performed by automated equipment. It is also understood by the skilled person that one or more steps of the method, e.g. the step of estimating the amount of electrons liberated or consumed by the chemistry matrix may be repeated.

The term "determining" relates to measuring of the amount of an analyte in a sample, typically semi-quantitatively or, more typically, quantitatively.

Methods of estimating the amount of redox equivalents, typically electrons, liberated or consumed in a chemistry matrix are known from the prior art. Typically, the amount of redox equivalents liberated or consumed is estimated by means of an optical or by an electrochemical test element. Typically, estimating the amount of redox equivalents liberated or consumed comprises contacting at least two electrodes with the chemistry matrix or with means conductively connected to said test chemistry, applying a voltage to said electrodes and measuring current flowing through said electrodes contacting the chemistry matrix.

The present invention further relates to a kit for determining the amount of an analyte in a sample, comprising:
a) a test element according to the present invention and
b) a means for creating an incision on a bodily surface of a subject.

Means for creating an incision on a bodily surface are known to the skilled person and include, typically, scalpels, knives, or needles. More typical means for creating an incision on a bodily surface are lancets.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Further optional features and embodiments of the invention will be disclosed in more detail in the subsequent description of typical embodiments, typically in conjunction with the dependent claims. Therein, the respective optional features may be realized in an isolated fashion as well as in any arbitrary feasible combination, as the skilled person will realize. The scope of the invention is not restricted by the typical embodiments.

In the Figures:

FIG. 1.) cyclic voltammograms of 1-(3-Carboxy-propionylamino)-5-ethyl-phenazinium (compound of formula (III)). A: Buffer pH 7.0 (blank current), B: 2 mM 1-(3-Carboxy-propionylamino)-5-ethyl-phenazinium in buffer, C: 2 mM 1-(3-Carboxy-propionylamino)-5-ethyl-phenazinium+1.2 mM ascorbic acid in buffer, D: 1.2 mM ascorbic acid in buffer.

Figure 2A:
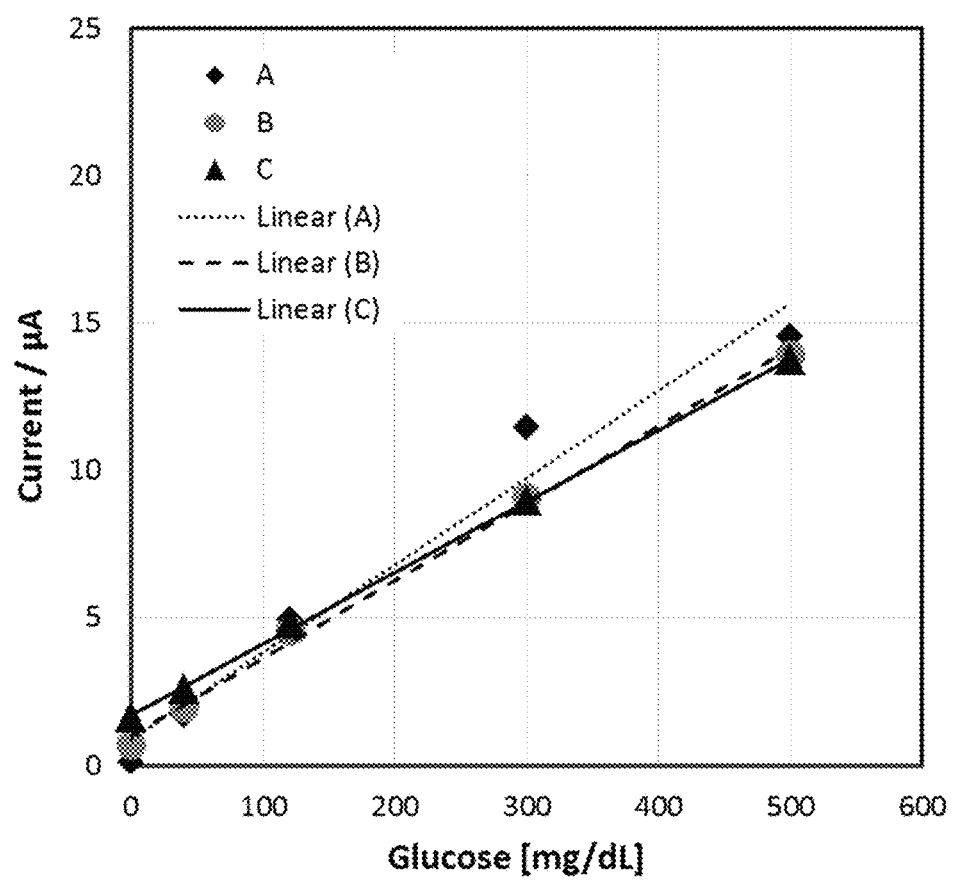
Figure 2B:
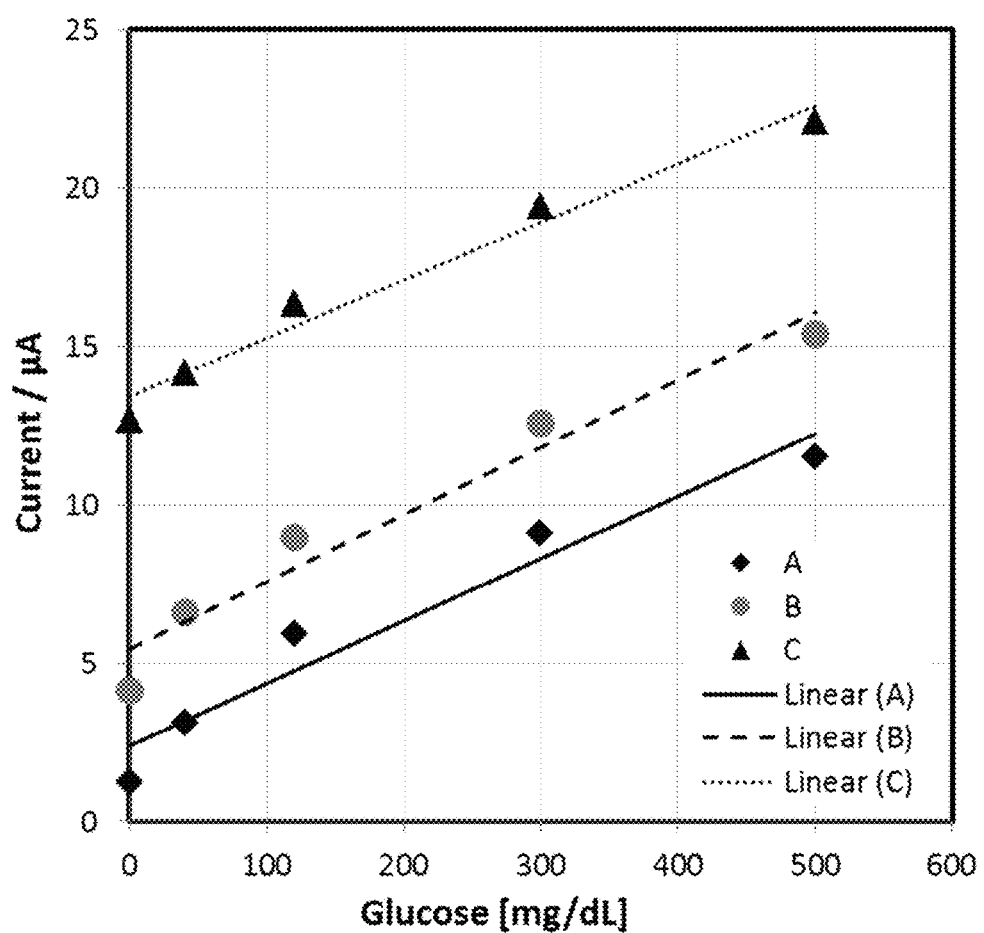

FIG. 2A.) dose response curve of ascorbic acid interference; Chronoamperometry at −100 mV, pH 7.0; solution of 5 mM 1-(3-Carboxy-propionylamino)-5-ethyl-phenazinium, 35 mM cNAD, and 1.5 kU/g glucose dehydrogenase (GDH) was incubated with the glucose concentrations indicated. A: 0 mg/mL ascorbic acid, B: 30 mg/mL ascorbic acid, C: 100 mg/mL ascorbic acid; Linear: linear regression;

FIG. 2B.) dose response curve of ascorbic acid interference; Chronoamperometry at +650 mV, pH 7.0; solution of 5 mM 1-(3-Carboxy-propionylamino)-5-ethyl-phenazinium, 35 mM cNAD, and 1.5 kU/g glucose dehydrogenase (GDH) was incubated with the glucose concentrations indicated, A: 0 mg/mL ascorbic acid, B: 30 mg/mL ascorbic acid, C: 100 mg/mL ascorbic acid; Linear: linear regression.

Figure 3:
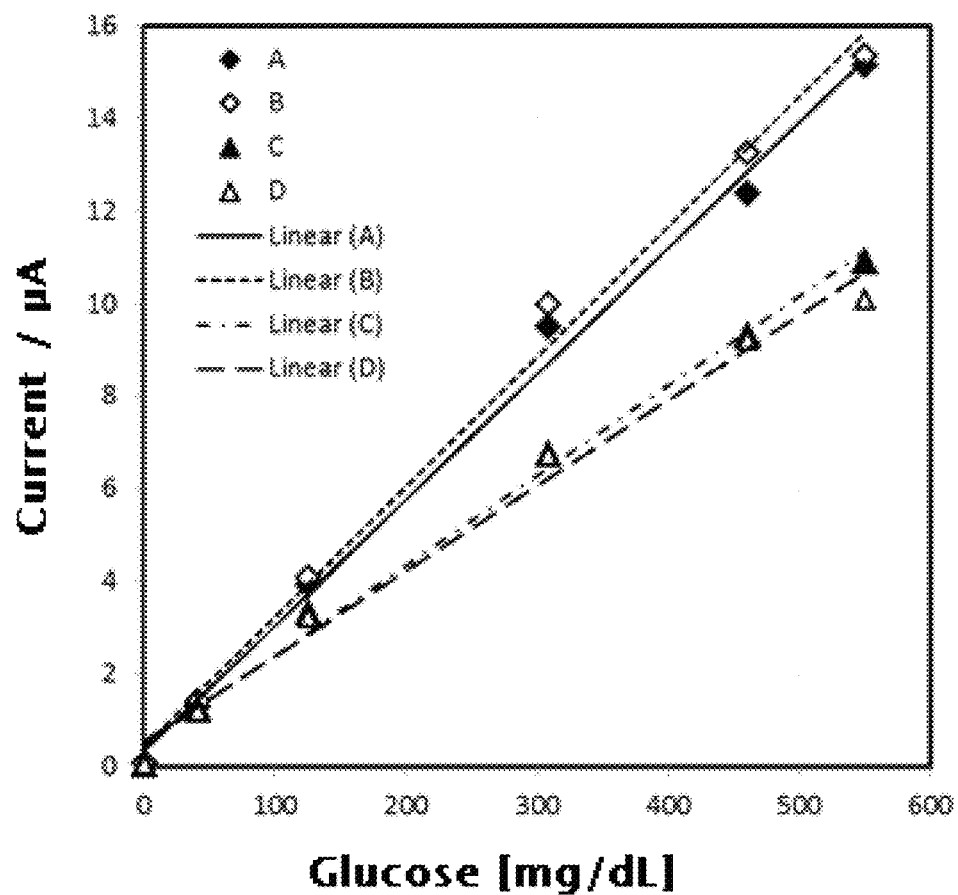

FIG. 3.) Pot life of mediator formulations. Mediators 1-(3-Carboxy-propionylamino)-5-ethyl-phenazinium and 1-(3-Carboxypropoxy)-5-ethylphenazinium were compared in a pot life experiment. Pot life of 1-(3-Carboxy-propionylamino)-5-ethyl-phenazinium (A: 0 h, B: 48 h) and 1-(3-Carboxypropoxy)-5-ethylphenazinium (C:=0 h, D: 48 h) are shown; Linear: linear regression.

Figure 4A:
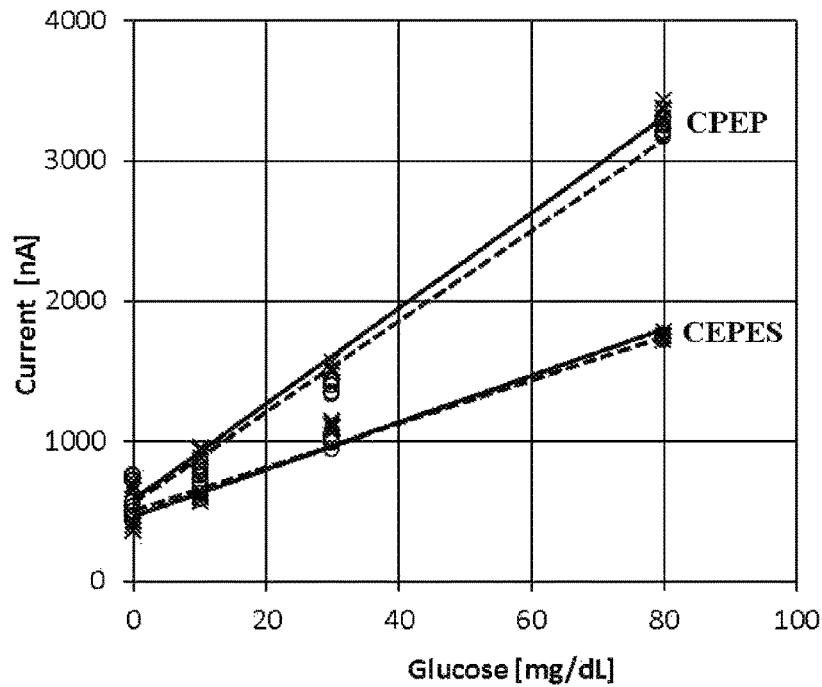

FIG. 4A.) Dose response curves for 1-(3-Carboxy-propionylamino)-5-ethyl-phenazinium (CPEP) and for 1-(3-Carboxypropoxy)-5-ethylphenazinium (CEPES) in glucose measurement strips. Shown are linear regression lines for five replicas in the absence of ascorbate (full lines) and in the presence of ascorbate (dashed lines). $R^2$ for 1-(3-Carboxypropionylamino)-5-ethyl-phenazinium was 0.9962 in the absence of ascorbate and was 0.9834 in the presence of ascorbate. $R^2$ for 1-(3-Carboxypropoxy)-5-ethyl-phenazinium was 0.9728 in the absence of ascorbate and was 0.999 in the presence of ascorbate.

Figure 4B:
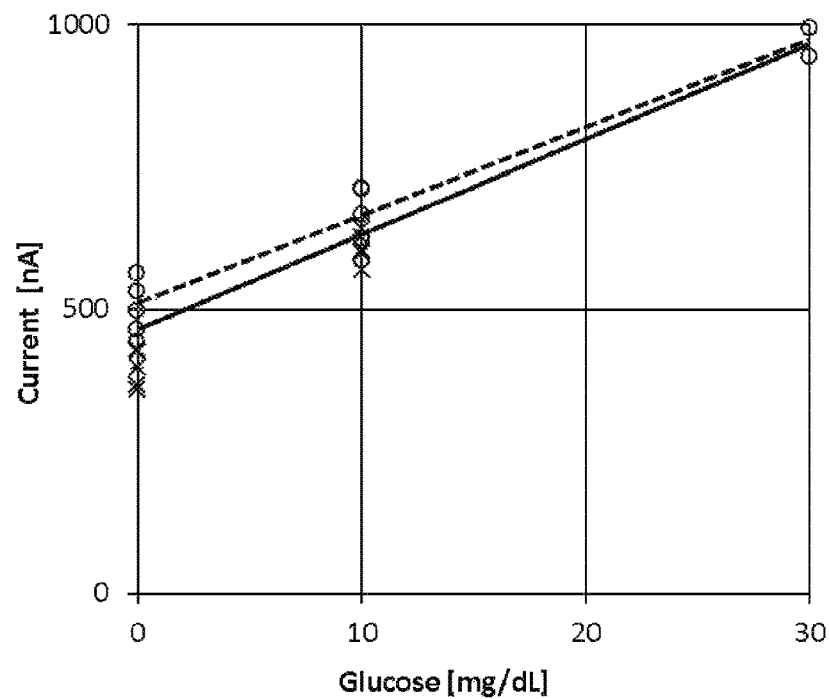

FIG. 4B.) Current offset caused by ascorbate with 1-(3-Carboxypropoxy)-5-ethylphenazinium (CEPES) in glucose measurement strips at low glucose concentrations; same data as in (A), detail view of values measured with CEPES at low glucose concentrations.

DETAILED DESCRIPTION OF THE EMBODIMENTS (EXAMPLES)

Key intermediates for the synthesis of compounds according to the invention are 1-amino phenazines, which can be synthesized by various methods (see Urleb, U. and Gobec, S., Science of Synthesis, 2004, 16, 913-943). 1-amino phenazine is then reacted with an acyl- or sulfonylchloride and alkylated, optionally after removal of a protecting group. For phenazinium salts with an aryl group on the phenazinium nitrogen, a different synthesis method can be used, see Kehrmann and Masslenikow; Chemische Berichte, 1911, 44, 2629.

Example 1: Synthesis of 1-amino-phenazine

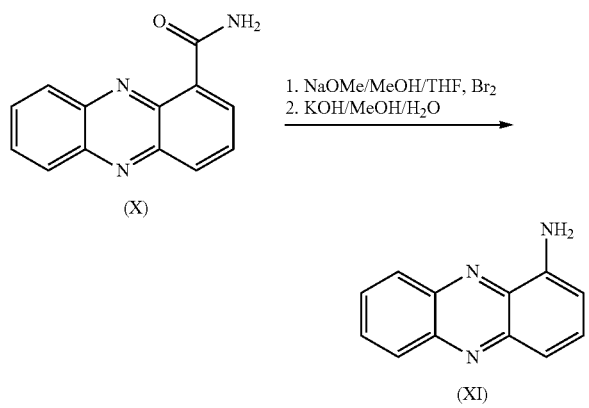

A solution of sodium methanolate (25% in MeOH, 24.6 ml, 107 mmol) in 100 ml MeOH was cooled to −78° C. and a solution of bromine (2.10 ml, 40.9 mmol) in 10.0 ml MeOH was added over a period of 2 min. Under further cooling the solution was first stirred 5 min followed by the addition of phenazine-1-carboxamide (4.00 g, 17.9 mmol) in 200 ml dry methanol and 400 ml dry THF over a period of 1 h via dropping funnel. After the complete addition a clear orange solution was obtained that was warmed to room temperature and further stirred 2 h at 55° C. Following the mixture was cooled down to room temperature and stirred further 72 h. After evaporating under reduced pressure the residue was dissolved in methanol (300 ml) and aqueous NaOH (40%, 150 ml) and refluxed for 4 h at 90° C. Subsequently the solution was cooled down to 0° C. and set to pH 8.5 with concentrated HCl, obtaining a dark red suspension. After concentrating to about 200 ml under reduced pressure 500 ml water was added. The mixture was extracted three times with CHCl₃. The combined organic layers were dried over Na₂SO₄ and concentrated under reduced pressure. The crude product was purified by silica gel chromatography (n-hexane/ethyl acetate, 80:20→75:25) obtaining 2.86 g (82%) of the title compound as dark red solid.

Example 2: Synthesis of N-phenazine-1-yl-succinamic acid methyl ester

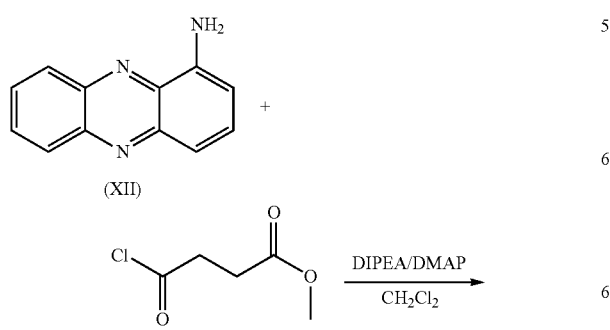

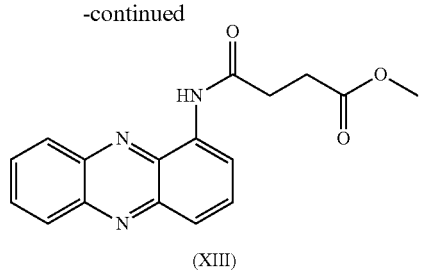

1-Aminophenazine (1.00 g, 5.12 mmol) was dissolved in 40.0 ml CH₂Cl₂ and N,N-diisopropylethylamine (957 μl, 5.63 mmol). After addition of 4-N,N-dimethylaminopyridine (31.3 mg, 0.256 mmol) the mixture was cooled to 0° C., followed by the addition of methyl 4-chloro-4-oxobutyrate (693 μl, 5.63 mmol) over a period of 5 min. The resulting solution was further stirred for 16 h at room temperature. After diluting with 50.0 ml CH₂Cl₂ the mixture was washed once with 50.0 ml aqueous NaOH (0.5%). The organic layer was dried over Na₂SO₄ and concentrated under reduced pressure. The crude product was purified by silica gel chromatography (n-hexane/acetone 80:20) obtaining 1.45 g (92%) of the title compound as yellow solid.

Example 3: Synthesis of 1-(3-Carboxy-propionylamino)-5-ethyl-phenazinium trifluoroacetate

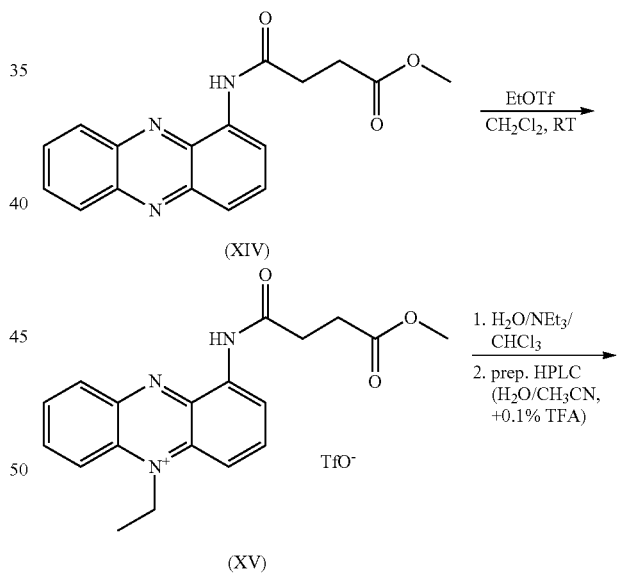

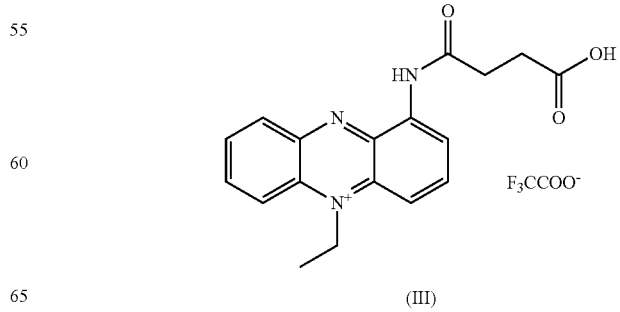

Ethyl trifluoromethanesulfonate (542 µl, 4.18 mmol) was added dropwise to a solution of N-Phenazin-1-yl-succinamic acid methyl ester (64.6 mg, 0.208 mmol) in 2.00 ml CH$_2$Cl$_2$. Subsequently the mixture was refluxed 3.5 h at 50° C. and stirred 16 h at room temperature. Then 50.0 ml CH$_2$Cl$_2$ and 2.00 ml NEt$_3$ were added and the resulting solution was extracted two times with water. The combined aqueous layers were washed once with CHCl$_3$ and lyophilized to obtain 42.0 mg crude product. This was purified by preparative HPLC (Chromolith, H$_2$O/CH$_3$CN gradient+0.1% TFA) resulting 28.9 mg (43%) of the title compound as dark purple crystals.

Example 4: Synthesis of N-Phenazin-1-yl-methanesulfonamide

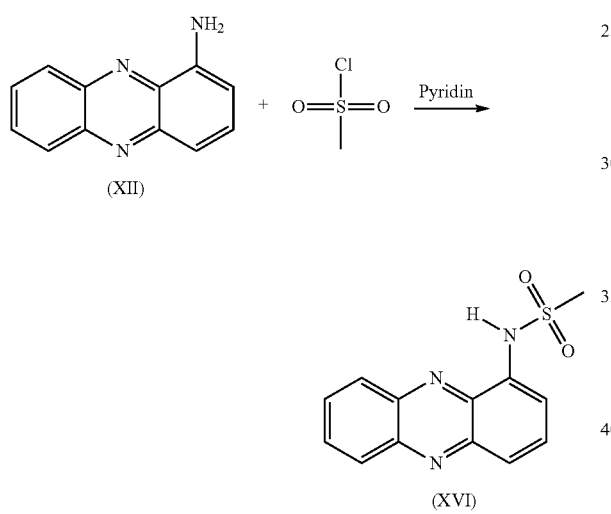

1-Amino-phenazine (50.0 mg, 0.256 mmol) was diluted in pyridine (1.00 ml) and cooled to 0° C. Under further cooling methanesulfonyl chloride (23.8 µl, 0.307 mmol) was added. The mixture was stirred 5 min at 0° C. and subsequently 16 h at room temperature. After concentrating under reduced pressure, the crude product was purified by silica gel chromatography (n-hexane/acetone 80:20) obtaining 66.0 mg (94%) of the title compound as yellow solid.

Example 5: Synthesis of 5-Ethyl-1-methanesulfonylamino-phenazinium trifluoracetate

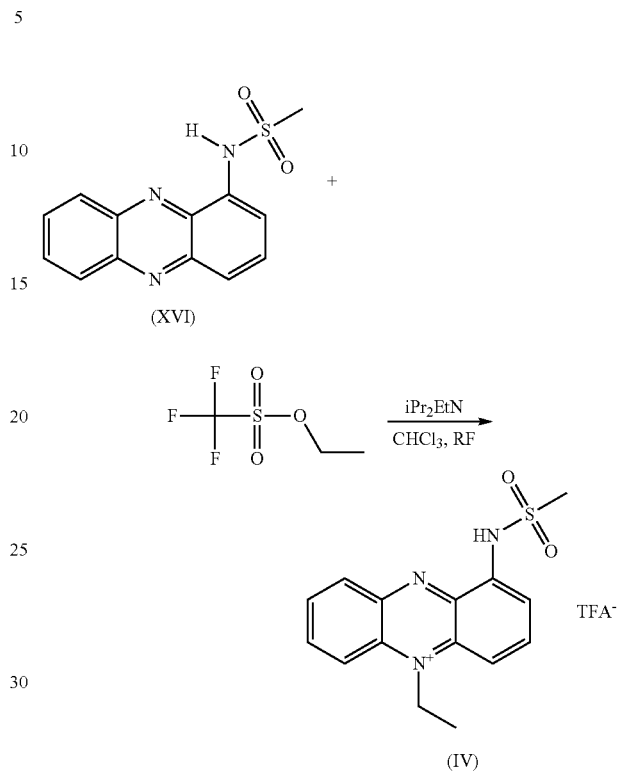

N-Phenazin-1-yl-methanesulfonamide (20.0 mg, 0.073 mmol) was diluted in CHCl$_3$ (2.00 ml) and ethyl trifluormethanesulfonate (1.00 ml, 7.70 mmol) was added turning the mixture red immediately. The mixture was refluxed at 70° C. for 7 h and stirred at room temperature for 16 h. Then N-Ethyldiisopropylamine (250 µl, 1.46 mmol) was added turning the color from dark red to brown. This mixture was further refluxed for 8 h and stirred at room temperature for 16 h. The crude product obtained after concentrating under reduced pressure was diluted in 10.0 ml CHCl$_3$ and 10.0 ml water. The organic layer was extracted four times with water. The combined aqueous layers were reduced to dryness and purified over preparative HPLC (Chromolith; H$_2$O/TFA-gradient+0.1% TFA) obtaining 2.2 mg (7%) as dark blue solid.

Example 6: Synthesis of Decanedioic acid bis-phenazin-1-ylamide bistrifluoroacetate salt

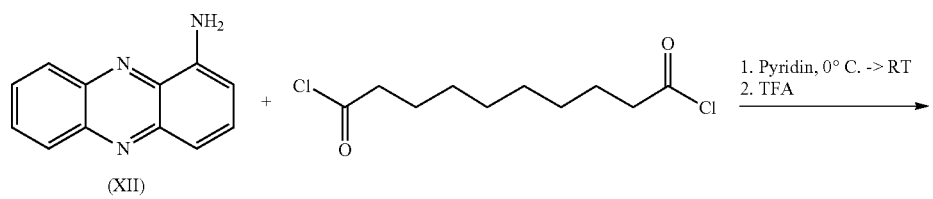

-continued

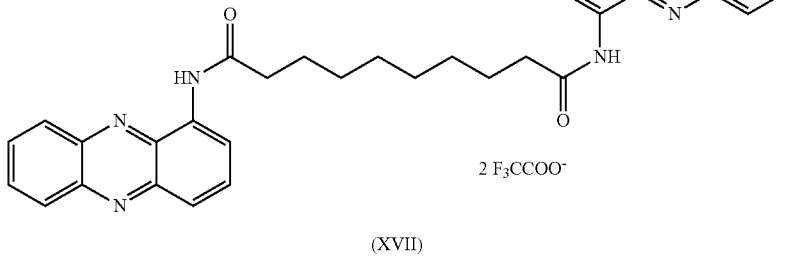

(XVII)

1-Amino-phenazine (25.0 mg, 0.128 mmol) was dissolved in pyridine (1.30 ml) and cooled to 0° C. To this solution sebacoyl chloride (13.7 µl, 0.064 mmol) in 0.50 ml $CH_2Cl_2$ was added slowly over a period of 30 min. The resulting suspension was further stirred 48 h at room temperature. Following the mixture was diluted with triethylammonium acetate buffer (pH 7, 1M, 5.00 ml) and extracted three times with $CH_2Cl_2$. The combined organic layers were dried over $Na_2SO_4$ and concentrated under reduced pressure.

The obtained crude product was suspended in 3.00 ml $H_2O/CH_3CN$ (1:1+0.1% TFA) and filtered. The residue, mainly containing the title compound was used without further purification. Yield: 12.3 mg (34%) as yellow solid.

Example 7: Synthesis of Decanedioic acid bis-[(5-ethyl-phenazin-1-yl)-amide

To a suspension of decanedioic acid bis-phenazin-1-ylamide ditrifluoroacetate salt (12.3 mg, 0.016 mmol) in $CH_2Cl_2$ (3.00 ml) was added diisopropylethylamine (37.4 µl, 0.22 mmol) and ethyl trifluoromethanesulfonate (300 µl, 2.31 mmol). The resulting brown solution was refluxed 3 h at 55° C. and further stirred for 16 h at room temperature. After evaporating under reduced pressure the obtained crude product was purified by preparative HPLC (XTerra, $H_2O$/$CH_3CN$ gradient+0.1% TFA), yielding 0.9 mg (9%) of the title compound as dark purple crystals.

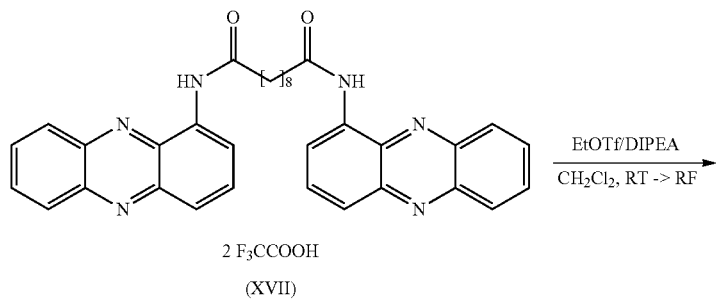

(XVII)

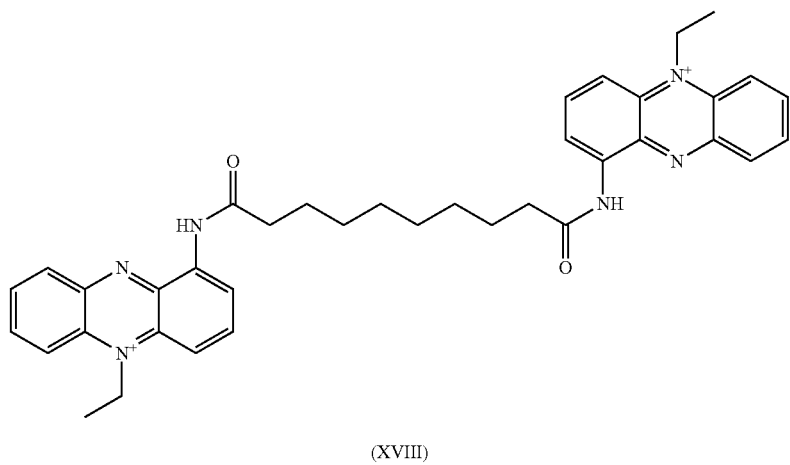

(XVIII)

Example 8: Synthesis of Pentanedioic acid bis-phenazin-1-ylamide

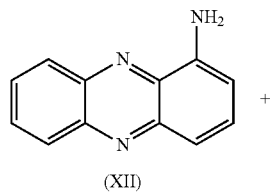

(XII)

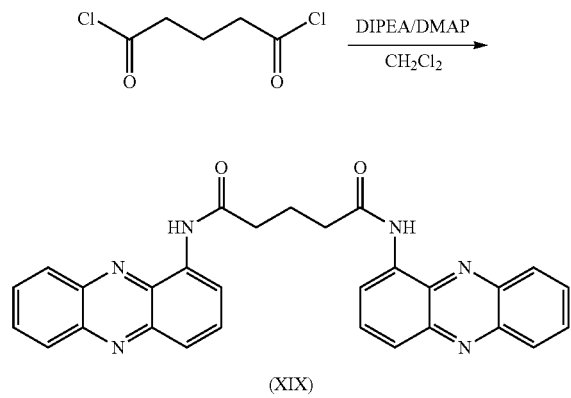

(XIX)

To a solution of 1-Amino phenazine (50.0 mg, 0.256 mmol) was added diisopropyl ethylamine (87.0 μl, 0.512 mmol) and a catalytically amount of dimethylaminopyridine. To the resulting red solution glutaryl chloride (16.3 μl, 0.128 mmol) was added and stirred for 16 h at room temperature. The obtained orange suspension was diluted with water and extracted two times with $CH_2Cl_2$. The combined organic layers were dried over $Na_2SO_4$ and concentrated under reduced pressure. The resulting crude product was suspended in acidic acid and filtered. The obtained residue was further purified by silica gel chromatography ($CHCl_3$/acetone, 9:1) yielding 15.8 mg (13%) of the title compound as yellow solid.

Example 9: Synthesis of 5-Ethyl-1-[4-(phenazin-1-ylcarbamoyl)-butyrylamino]-phenazinium trifluoroacetat

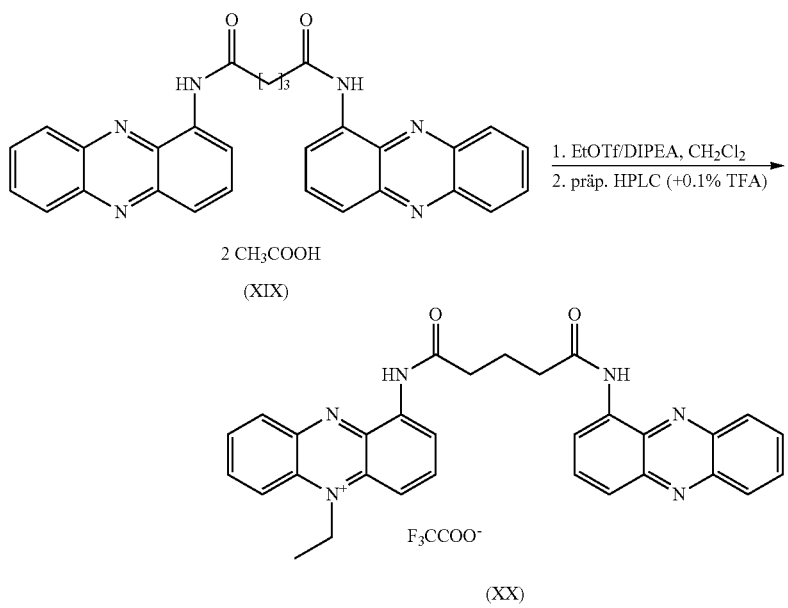

Pentanedioic acid bis-phenazin-1-ylamide diacetate salt (15.8 mg, 0.032 mmol) was suspended in $CH_2Cl_2$ (3.00 ml) and added with ethyl triflate (500 μl, 3.86 mmol). Diisopropyl ethylamine (48.9 μl, 0.288 mmol) was added to the resulting red brown suspension followed by refluxing for 1.5 h at 50° C. After 16 h stirring at room temperature the mixture was refluxed again for 7 h followed by further stirring at room temperature for 16 h. The resulting clear purple solution was concentrated under reduced pressure. The obtained crude product was suspended in 3.00 ml $H_2O/CH_3CN$ (1:1+0.1% TFA) and filtered. The residue was further purified by preparative HPLC (XTerra, $H_2O/CH_3CN$ gradient+0.1% TFA), yielding 1.0 mg (6%) of the title compound as redbrown solid.

Example 10: Redox Potential of 1-(3-Carboxy-propionylamino)-5-ethyl-phenazinium The formal redox potential of a typical 1-Acylated amino phenazinium ethosulfate, 1-(3-Carboxy-propionylamino)-5-ethyl-phenazinium (compound of formula (III)), was measured vs. Ag/AgCl at a gold working electrode in a test strip. We obtained −236 mV vs. Ag/AgCl under physiological conditions (0.9% NaCl) by cyclic voltammetry, shown in FIG. 1. The cyclic voltammograms show, that a relatively low potential of −100 mV vs. Ag/AgCl is sufficient in order to oxidize the substance.

The quasi reversible oxidation and reduction of the mediator 1-(3-Carboxy-propionylamino)-5-ethyl-phenazinium occurs in a potential range between 0 mV and −500 mV vs. Ag/AgCl via two electron transfer. Ascorbic acid cannot be oxidized in this potential window and the current is similar to the blank current of the pure buffer solution. Adding ascorbic acid to the mediator 1-(3-Carboxy-propionylamino)-5-ethyl-phenazinium does not significantly change the anodic and cathodic currents and the redox potential is just shifted to −231 mV vs. Ag/AgCl. Therefore, the addition of ascorbic acid does not significantly reduce the redox mediator.

Example 11: Ascorbate Interference with 1-(3-Carboxy-propionylamino)-5-ethyl-phenazinium FIG. 2 shows the advantage of the low oxidation potential of −100 mV using the redox mediator 1-(3-Carboxy-propionylamino)-5-ethyl-phenazinium in comparison to the direct oxidation of cNADH at +650 mV. At the latter potential the ascorbic acid will be oxidized too and the blank current increases rapidly depending on the concentration of ascorbic acid. Therefore, the relatively low potential of −100 mV is very useful in order to avoid a direct oxidation of interfering substances and the blank current remains very close to zero even though the sample contains high concentrations of ascorbic acid. Currents were measured under conventional conditions (pH 7.0) in the presence of cNAD (35 mM), glucose dehydrogenase (1.5 kU/g) at various concentrations of ascorbate and glucose.

Example 12: Pot Life of 1-(3-Carboxy-propionylamino)-5-ethyl-phenazinium and 1-(3-Carboxy-propoxy)-5-ethylphenazinium Mediators 1-(3-Carboxy-propionylamino)-5-ethyl-phenazinium and 1-(3-Carboxypropoxy)-5-ethyl-phenazinium were compared in a pot life experiment. Performance of mediators was measured immediately after preparing the reaction mixture (t=0) and after 48 h. As shown in FIG. 3, both redox mediators show no significant decrease in current after 48 hours of pot life. Therefore, both mediators seem to be very stable in a formulation. The mediator 1-(3-Carboxy-propionylamino)-5-ethyl-phenazinium shows higher currents than the mediator 1-(3-Carboxypropoxy)-5-ethylphenazinium over the entire range of glucose concentrations.

Example 13: Ascorbate Interference with other 1-amino-penazine derivatives

1-Acetylamino-5-methyl-phenazinium trifluormethanesulfonate, 1-Acetylamino-5-ethyl-phenazinium trifluoroacetate, and 1-(3-Carboxy-propionylamino)-5-ethyl-phenazinium (formula III) were compared regarding their reactivity towards ascorbate. To this end, each 0.23 mM of the respective compound was incubated at room temperature in 0.1 M triethylammonium acetate buffer (pH 7) in the presence of a 5 fold molar excess of ascorbate. Decrease of absorption at 517 nm (1-(3-Carboxy-propionylamino)-5-ethyl-phenazinium) or 512 nm (other two compounds) was recorded over time. Whereas with 1-Acetylamino-5-methyl-phenazinium, the absorption decreased by 12% per minute, the decrease slowed to 7% per minute for 1-Acetylamino-5-ethyl-phenazinium, and to less than 5% for 1-(3-Carboxy-propionylamino)-5-ethyl-phenazinium.

Example 14: Performance and Ascorbate Interference with 1-hydroxy-phenazine derivatives 1-(3-Carboxypropoxy)-5-ethylphenazinium and 1-(3-Carboxy-propionylamino)-5-ethyl-phenazinium were compared regarding their performance as redox mediators in glucose test strips in the absence and in the presence of ascorbate. To this end, dose response curves were recorded with glucose concentrations of 0 mg/dL, 10 mg/dL (0.5 mM), 30 mg/dL (1.5 mM), and 80 mg/dL (4.0 mM) and in the presence of 1.48 mM of either redox mediator. Ascorbic acid, if present, was used at a concentration of 15 mg/dL (0.85 mM). As shown in FIG. 4A), the dose response at a given glucose concentration is higher with 1-(3-Carboxy-propionylamino)-5-ethyl-phenazinium (CPEP) as compared to 1-(3-Carboxypropoxy)-5-ethylphenazinium (CEPES). Also, the slope dose response is approximately twofold for 1-(3-Carboxy-propionylamino)-5-ethyl-phenazinium as compared to 1-(3-Carboxypropoxy)-5-ethylphenazinium (34 nA*dL/mg vs. 16.7 nA*dL/mg). Moreover, ascorbate only has a small effect on the currents measured in the presence of 1-(3-Carboxy-propionylamino)-5-ethyl-phenazinium. In contrast, ascorbate causes a current offset at low glucose concentrations, in particular below 30 mg/dL when 1-(3-Carboxypropoxy)-5-ethylphenazinium is used as a redox mediator (FIG. 4B)).

The invention claimed is:

1. A chemical compound or a salt or solvate thereof comprising the structure (I)

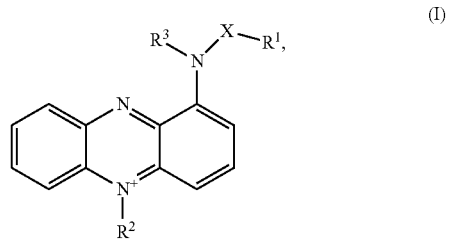

wherein
X is —C(=O)—, —C(=S)—, or —S(=O)$_2$—,
R$^1$ is an organic side chain comprising at least 2 C-atoms if X is C(=O), and at least 1 C-atom if X is C(=S) or S(=O)$_2$,
R$^2$ is an organic side chain comprising at least 2 C-atoms,
R$^3$ is H or an organic side chain, and
wherein at least one of R$^1$, R$^2$ and R$^3$ is a hydrophilic side chain, wherein said hydrophilic side chain is a side chain comprising at least one hydrophilic functional group selected from the groups consisting of —C(=Y$^1$)—OH, —C(OH) R$^{11}$R$^{12}$, —C(=Y$^1$)—R$^{11}$, —C(=Y$^1$)—Y$^2$—R$^{11}$, —Y$^1$—R$^{11}$, —NH$_2$, —NHR$^{11}$, —NMe$^{3+}$, —NH—C(=Y$^1$)—R$^{11}$, —S(O)R$^{11}$, —SO$_2$R$^{11}$, —SO$_2$—OH—, and —P(O)OR$^{11}$)(OR$^{12}$) —O—P(O)(OR$^{11}$)(OR$^{12}$); with Y$^1$ and Y$^2$ being independently selected from O or S and with R$^{11}$ and R$^{12}$ being, independently of each other, selected from the group consisting of H and, unsubstituted or substituted, alkyl and aryl.

2. The chemical compound according to claim 1, wherein the at least one hydrophilic functional group is —C(=O)—R$^{11}$ or —C(=O)—OH.

3. The chemical compound according to claim 1, wherein R$^1$ is alkyl with a contiguous chain of 3 to 8 C-atoms covalently bound to the C or S atom of group X, comprising at least one substituent independently selected from OH, $OPO_3^{2-}$, $PO_3^{2-}$, $SO_3^-$, and $COO^-$.

4. The chemical compound according to claim 1, wherein $R^2$ has the structure $—(CH_2)_n—CH_3$ with n being in the range of from 0 to 6.

5. The chemical compound according to claim 4, with n being 0, 1 or 2.

6. The chemical compound according to claim 5, wherein $R^2$ is ethyl.

7. The chemical compound according to claim 1, having the structure (II)

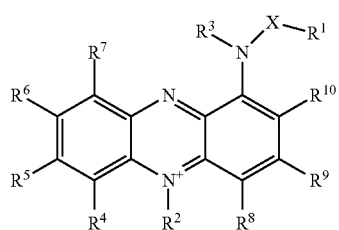
(II)

wherein $R^4$, $R^3$, $R^6$, $R^7$, $R^8$, $R^9$ and $R^{10}$ are, independently of each other, selected from the group consisting of H; substituted or unsubstituted alkyl, cycloalkyl, alkenyl, cycloalkenyl, alkinyl, aryl, heterocycloalkyl, heteroaryl, halogen; $—NO_2$, $—SO_3^-$ $—CN$, $—CH=CH—COOH$, and $—Y^3—R^{13}$ with $Y^3$ being $—O—$, $—C(=O)—$ or $—N(R^{14})—$, with $R^{13}$ and $R^{14}$ being, independently of each other, selected from the group consisting of unsubstituted or substituted, alkyl and aryl.

8. The chemical compound according to claim 5, wherein $R^3$, $R^4$, $R^6$, $R^7$, $R^8$, $R^9$ and $R^{10}$ are —H.

9. The chemical compound according to claim 1 comprising one of the following structures:

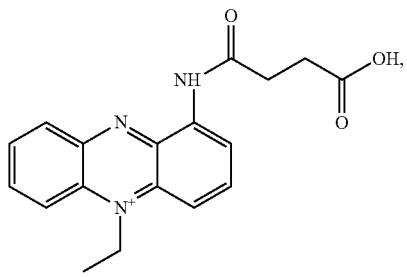
(III)

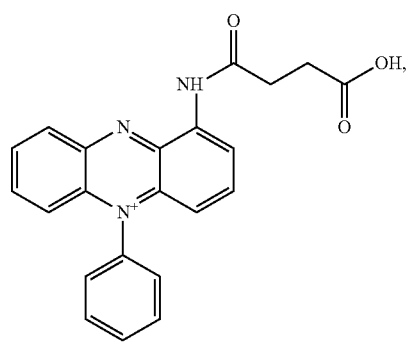
(V)

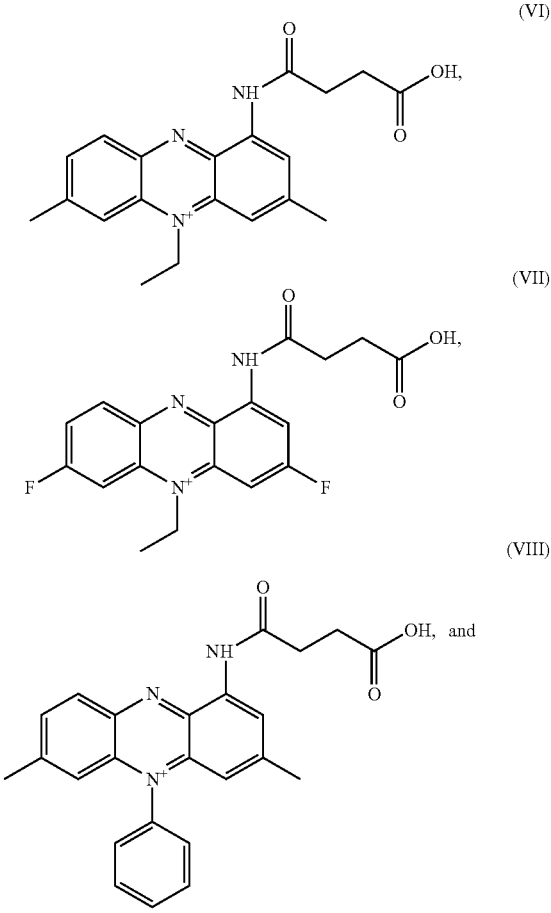
(VI)

(VII)

(VIII)

(IX)

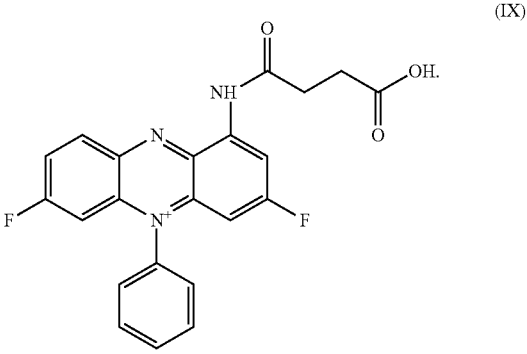

10. The chemical compound according to claim 1 consisting of one of the following structures:

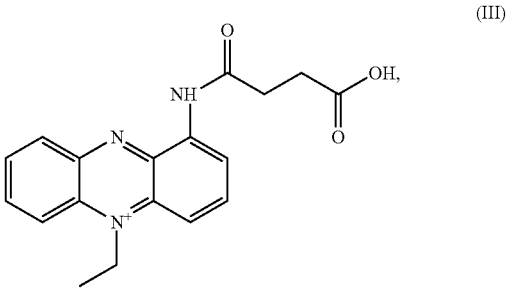
(III)

-continued

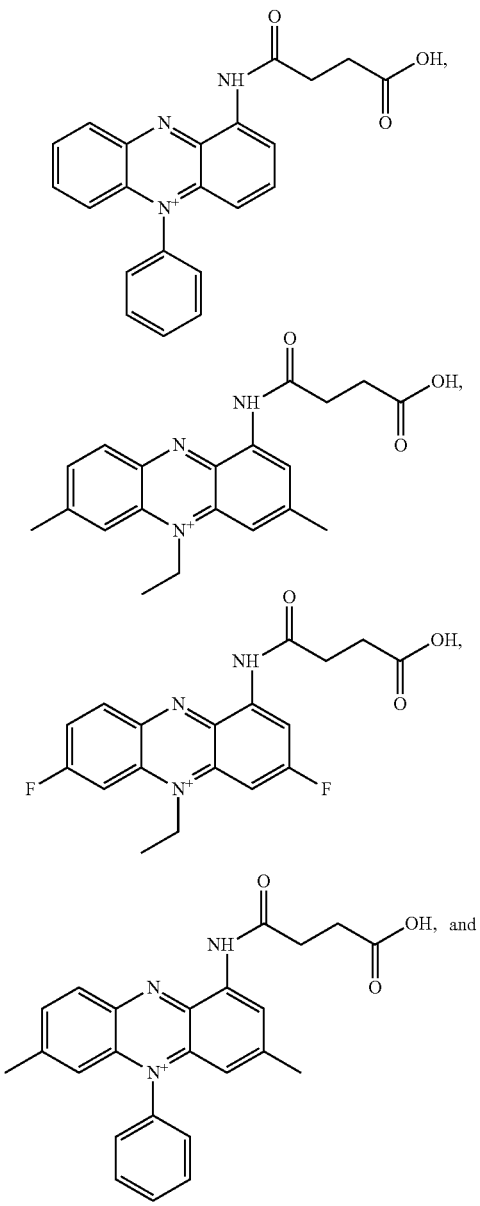

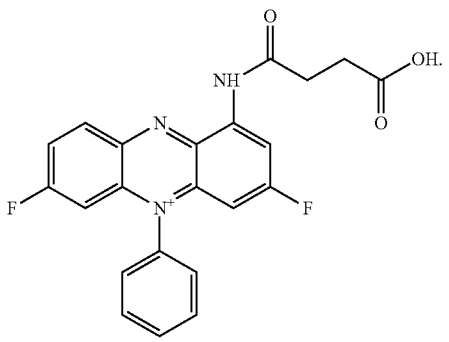 [SMILES: Cc1ccc2nc3c(NC(=O)CCC(=O)O)cc(C)cc3[n+](-c3ccccc3)c2c1]

11. A chemistry matrix comprising the chemical compound of claim 1.

12. A test element comprising the chemical compound of claim 1.

13. A test element comprising the chemistry matrix of claim 11.

14. A method for determining the amount of an analyte in a sample, comprising
   a) contacting said sample with a chemistry matrix according to claim 11,
   b) estimating the amount of redox equivalents liberated or consumed by the chemistry matrix in the presence of said liquid sample, and
   c) thereby determining the amount of an analyte in a liquid sample.

15. The method of claim 14, wherein the amount of redox equivalents liberated or consumed by the chemistry matrix in step b) is estimated by means of an optical or by an electrochemical sensor.

* * * * *